US010920195B2

(12) United States Patent
Amendt et al.

(10) Patent No.: US 10,920,195 B2
(45) Date of Patent: Feb. 16, 2021

(54) METHODS TO GENERATE EPITHELIAL CELLS

(71) Applicant: UNIVERSITY OF IOWA RESEARCH FOUNDATION, Iowa City, IA (US)

(72) Inventors: Brad A. Amendt, Iowa City, IA (US); Thad Sharp, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 307 days.

(21) Appl. No.: 15/526,282

(22) PCT Filed: Aug. 13, 2015

(86) PCT No.: PCT/US2015/045139
§ 371 (c)(1),
(2) Date: May 11, 2017

(87) PCT Pub. No.: WO2016/076929
PCT Pub. Date: May 19, 2016

(65) Prior Publication Data
US 2017/0321190 A1 Nov. 9, 2017

Related U.S. Application Data

(60) Provisional application No. 62/079,260, filed on Nov. 13, 2014.

(51) Int. Cl.
*C12N 5/077* (2010.01)
*A61K 35/28* (2015.01)

(52) U.S. Cl.
CPC ............ *C12N 5/0652* (2013.01); *A61K 35/28* (2013.01); *C12N 2501/60* (2013.01); *C12N 2501/602* (2013.01); *C12N 2501/65* (2013.01); *C12N 2501/998* (2013.01); *C12N 2506/13* (2013.01)

(58) Field of Classification Search
CPC combination set(s) only.
See application file for complete search history.

(56) References Cited

U.S. PATENT DOCUMENTS

| | | |
|---|---|---|
| 4,559,157 A | 12/1985 | Smith et al. |
| 4,608,392 A | 8/1986 | Jacquet et al. |
| 4,820,508 A | 4/1989 | Wortzman |
| 4,938,949 A | 7/1990 | Borch et al. |
| 4,992,478 A | 2/1991 | Geria |
| 5,350,674 A | 9/1994 | Boenisch et al. |
| 5,585,362 A | 12/1996 | Schwarz et al. |
| 2006/0211004 A1 | 9/2006 | Ilsley et al. |
| 2007/0044164 A1 | 2/2007 | Dickins et al. |
| 2012/0121548 A1 | 5/2012 | Itescu |
| 2013/0216554 A1 | 8/2013 | Talchai et al. |
| 2015/0023934 A1* | 1/2015 | Ionas ............... C12N 5/0684 424/93.21 |

OTHER PUBLICATIONS

Neff et al. "Dedifferentiation and the role of sall4 in reprogramming and patterning during amphibian limb regeneration." Dev Dyn. May 2011;240(5):979-89. (Year: 2011).*
Lavial et al. "Chicken embryonic stem cells as a non-mammalian embryonic stem cell model." Dev Growth Differ. Jan. 2010;52(1):101-14. (Year: 2010).*
Ma et al. "Bioinformatic analysis of the four transcription factors used to induce pluripotent stem cells." Cytotechnology. Dec. 2014;66(6):967-78 (Year: 2014).*
Cox and Rizzino "Induced pluripotent stem cells: what lies beyond the paradigm shift." Exp Biot Med (Maywood). Feb. 2010;235(2):148-58. (Year: 2010).*
Toro et al. "Cell-specific activation of the atrial natriuretic factor promoter by PITX2 and MEF2A." J Biol Chem. Dec. 10, 2004;279(50):52087-94. (Year: 2004).*
Schnerch et al. "Distinguishing between mouse and human pluripotent stem cell regulation: the best laid plans of mice and men." Stem Cells. Mar. 31, 2010;28(3):419-30. (Year: 2010).*
Zhang, et al., "MicroRNAs Regulate Pituitary Development, and MicroRNA 26b Specifically Targets Lymphoid Enhancer Factor 1 (Lef-1), Which Modulates Pituitary Transcription Factor 1 (Pit-1) Expression", J Biol Chem 285, 34718-34728 (2010).
Korpal, et al., "The miR-200 family inhibits epithelial-mesenchymal transition and cancer cell migration by direct targeting of E-cadherin transcriptional repressors ZEB1 and ZEB2", J Biol Chem 283(22), 14910-14914 (2008).
Kratochwil, et al., "Lef1 expression is activated by BMP-4 and regulates inductive tissue interactions in tooth and hair development", Genes Dev 10, 1382-1394 (1996).
Li, et al., "E-cadherin regulates the behavior and fate of epithelial stem cells and their progeny in the mouse incisor", Developmental Biology 366(2), 357-366 (2012).
Limeback, et al., "Enamel protein and collagen production by cells subcultured from porcine tooth bud explants", Biochem Cell Biol 65, 698-709 (1987).

(Continued)

*Primary Examiner* — Titilayo Moloye
(74) *Attorney, Agent, or Firm* — Viksnins Harris Padys Malen LLP

(57) ABSTRACT

The invention provides in certain embodiments, a method of generating a re-programmed differentiated epithelial cell comprising (a) contacting a non-stem somatic cell obtained from a subject with an effective amount of a de-differentiation agent to form a de-differentiated cell, and (b) transfecting the de-differentiated cell with an expression cassette comprising a promoter operably linked to a nucleic acid encoding a conversion agent to form a re-programmed differentiated cell. The invention also provides in certain embodiments, a method of generating a re-programmed differentiated epithelial cell comprising (a) contacting a non-stem somatic cell obtained from a subject with an effective amount of a de-differentiation agent to form a de-differentiated cell, and (b) contacting the de-differentiated cell with a conversion agent to form a re-programmed differentiated cell. The invention provides in certain embodiments, re-programmed differentiated epithelial cells, and methods of using these re-programmed differentiated epithelial cells to repair or re-generate tissue in vivo.

11 Claims, 14 Drawing Sheets
Specification includes a Sequence Listing.

(56) References Cited

OTHER PUBLICATIONS

Lin, et al., "Pitx2 regulates lung asymmetry, cardiac positioning and pituitary and tooth morphogenesis", Nature 401(6750), 279-282 (1999).
Liu, et al., "Genetic dissection of Pitx2 in craniofacial development uncovers new functions in branchial arch morphogenesis, late aspects of tooth morphogenesis and cell migration", Development 130, 6375-6385 (2003).
Liu, et al., "Wnt/beta-catenin signaling directs multiple stages of tooth morphogenesis", Dev Biol 313, 210-224 (2008).
Liu, et al., "Wnt/β-catenin Signaling in Oral Tissue Development and Disease", J Dent Res 89, 318-330 (2010).
Logan, et al., "The Wnt signaling pathway in development and disease", Annual Review of Cell and Developmental Biology 20, 781-810 (2004).
Maas, et al., "The Genetic Control of Early Tooth Development", Crit Rev Oral Biol Med 8, 4-39 (1997).
Matsumura, et al., "Ameloblast-lineage cells of rat tooth germs proliferate and scatter in response to hepatocyte growth factor in culture", Int J Dev Biol 42, 1137-1142 (1998).
Menicanin, et al., "Identification of a common gene expression signature associated with immature clonal mesenchymal cell populations derived from bone marrow and dental tissues", Stem Cells Dev 19, 1501-1510 (2010).
Menicanin, et al., "Periodontal-Ligament-Derived Stem Cells Exhibit the Capacity for Long-Term Survival, Self-Renewal, and Regeneration of Multiple Tissue Types in Vivo", Stem Cells Dev 23, 1001-1011 (2014).
Michon, et al., "Tooth morphogenesis and ameloblast differentiation are regulated by micro-RNAs", Dev Biol 340, 355-368 (2010).
Mongroo, et al., "The role of the miR-200 family in epithelial-mesenchymal transition", Cancer Biology & Therapy 10, 219-222 (2010).
Morotomi, et al., "In vitro differentiation of dental epithelial progenitor cells through epithelial-mesenchymal interactions", Arch Oral Biol 50, 695-705 (2005).
Mucchielli, et al., "Mouse Otlx2/RIEG Expression in the Odontogenic Epithelium Precedes Tooth Initiation and Requires Mesenchyme-Derived Signals for Its Maintenance", Dev Biol 189, 275-284 (1997).
Mustonen, et al., "Lunatic Fringe, FGF, and BMP Regulate the Notch Pathway during Epithelial Morphogenesis of Teeth", Dev Biol 248, 281-293 (2002).
Nakahori, et al., "A human X-Y homologous region encodes "amelogenin"", Genomics 9(2), 264-269 (1991).
Neubuser, et al., "Antagonistic interactions between FGF and BMP signaling pathways: a mechanism for positioning the sites of tooth formation.", Cell 90, 247-255 (1997).
Noramly, et al., "beta-catenin signaling can initiate feather bud development", Development 126, 3509-3521 (1999).
Patent Cooperation Treaty, International Searching Authority, Search Report and Written Opinion for PCT/US2015/045139, 10 pages, dated Jan. 13, 2016.
Peters, et al., "Teeth: where and how to make them", Trends Genet 15, 59-64 (1999).
Saldanha, et al., "Java Treeview—extensible visualization of microarray data", Bioinformatics 20(17), 3246-3248 (2004).
Sasaki, et al., "LEF1 is a critical epithelial survival factor during tooth morphogenesis", Dev Biol 278, 130-143 (2005).
Sharp, et al., "A pituitary homeobox 2 (Pitx2):microRNA-200a-3p:β-catenin pathway converts mesenchymal cells to amelogenin-expressing dental epithelial cells", Journal of Biological Chemistry vol. 289 (39), 27327-27341 (2014).
Sharpe, et al., "Test-Tube Teeth", Sci Am 293, 34-41 (2005).
Shi, et al., "The efficacy of mesenchymal stem cells to regenerate and repair dental structures", Orthod Craniofacial Res 8(3), 191-199 (2005).
Snead, et al., "DNA sequence for cloned cDNA for murine amelogenin reveal the amino acid sequence for enamel-specific protein", Biochem Biophys Res Commun. 129, 812-818 (1985).
St. Amand, et al., "Antagonistic Signals between BMP4 and FGF8 Define the Expression of Pitx1 and Pitx2 in Mouse Tooth-Forming Anlage", Dev Biol 217, 323-332 (2000).
Stockinger, et al., "E-cadherin regulates cell growth by modulating proliferation-dependent β-catenin transcriptional activity", J Cell Biol 154, 1185-1196 (2001).
Tabata, et al., "Expression of cytokeratin 14 in ameloblast-lineage cells of the developing tooth of rat, both in vivo and in vitro", Arch Oral Biol 41, 1019-1027 (1996).
Tabata, et al., "Fibronectin Accelerates the Growth and Differentiation of Ameloblast Lineage Cells In Vitro", J Histochem Cytochem 51, 1673-1679 (2003).
Takahashi, et al., "Induction of pluripotent stem cells from mouse embryonic and adult fibroblast cultures by defined factors", Cell 126, 663-676 (2006).
Thesleff, et al., "Tooth morphogenesis and cell differentiation", Cur Opin Cell Biol 8(6), 844-850 (1996).
Trapnell, et al., "Differential gene and transcript expression analysis of RNA-seq experiments with TopHat and Cufflinks", Nat Protoc 7(3), 562-578 (2012).
Tucker, et al., "The cutting-edge of mammalian development; how the embryo makes teeth", Nat Rev Genet 5, 499-508 (2004).
Tummers, et al., "Observations on continuously growing roots of the sloth and the K14-Eda transgenic mice indicate that epithelial stem cells can give rise to both the ameloblast and root epithelium cell lineage creating distinct tooth patterns", Evol Dev 10, 187-195 (2008).
Tummers, et al., "Root or crown: a developmental choice orchestrated by the differential regulation of the epithelial stem cell niche in the tooth of two rodent species", Development 130, 1049-1057 (2003).
Vadlamudi, et al., "PITX2, β-catenin and LEF-1 interact to synergistically regulate the LEF-1 promoter", J Cell Sci 118, 1129-1137 (2005).
Venugopalan, et al., "Novel expression and transcriptional regulation of FoxJ1 during oro-facial morphogenesis", Hum Mol Genet 17, 3643-3654 (2008).
Wang, et al., "An Integrated Gene Regulatory Network Controls Stem Cell Proliferation in Teeth", Plos Biol. 5(6), e159 (2007).
Wellner, et al., "The EMT-activator ZEB1 promotes tumorigenicity by repressing stemness-inhibiting microRNAs", Nat Cell Biol 11, 1487-1495 (2009).
Xia, et al., "miR-200a Regulates Epithelial-Mesenchymal to Stem-like Transition via ZEB2 and β-Catenin Signaling", J Biol Chem 285, 36995-37004 (2010).
Yen, et al., "Regeneration of teeth using stem cell-based tissue engineering", Expert Opin Biol Ther 6, 9-16 (2006).
Yoo, et al., "MicroRNA-mediated conversion of human fibroblasts to neurons", Nature 476(7359), 228-231 (2011).
Zeichner-David, et al., "Control of ameloblast differentiation", Int J Dev Biol 39(1), 69-92 (1995).
Zhang, et al., "Fuz Regulates Craniofacial Development through Tissue Specific Responses to Signaling Factors", PLoS ONE 6, e24608, 16 pages (2011).
Zhang, et al., "Making a tooth: growth factors, transcription factors, and stem cells", Cell Res 15, 301-316 (2005).
Amen, et al., "Chromatin-associated HMG-17 is a major regulator of homeodomain transcription factor activity modulated by Wnt/β-catenin signaling", Nuc Acids Res 36, 462-476 (2008).
Amen, et al., "PITX2 and -Catenin Interactions Regulate Lef-1 Isoform Expression", Mol Cell Biol 27, 7560-7573 (2007).
Amendt, et al., "Control of Stem Cells Involved in Enamel Development by m microRNAs", Symposium: Mineralized State Control During Odontogenic Stem Cell Differentiation. International Association for Dental Research Meetings, Cape Town, South Africa, 18 pages, Jun. 2014.
Amendt, "microRNAs Regulate Conversion of Somatic Cells to Dental Cell Fates", Oral Session: Stem Cell Biology—Biology and Therapeutics of Stems Cells, International Associate for Dental Research Meetings, Cape Town, South Africa, 15 pages, Jun. 2014.

(56) References Cited

OTHER PUBLICATIONS

Amendt, et al., "microRNAs Regulate Conversion of Somatic Cells to Dental Cell Fates", 92nd General Session & Exhibition of the IADR Afric/Middle East Regional Meeting, Cape Town, South Africa, Abstract, Apr. 2014.
Amendt, et al., "Multifunctional Role of the Pitx2 Homeodomain Protein C-Terminal Tail", Mol Cel Biol. 19, 7001-7010 (1999).
Amendt, et al., "The Molecular Basis of Rieger Syndrome: Analysis of PITX2 Homeodomain Protein Activities", J Biol Chem 273, 20066-20072 (1998).
Bartel, "MicroRNAs: genomics, biogenesis, mechanism, and function", Cell 116, 281-297 (2004).
Bei, "Molecular Genetics of Tooth Development", Curr Opin Genet Dev 19, 504-510 (2009).
Blankenberg, et al., "Galaxy: a web-based genome analysis tool for experimentalists", Curr Protoc Mol Biol 0 19: Unit 19.1021, 33 pages (2010).
Brabletz, et al., "The ZEB/miR-200 feedback loop—a motor of cellular plasticity in development and cancer?", EMBO Reports 11(9), 670-677 (2010).
Brabletz, et al., "The ZEB1/miR-200 feedback loop controls Notch signalling in cancer cells", EMBO J 30, 770-782 (2011).
Burk, et al., "A reciprocal repression between ZEB1 and members of the miR-200 family promotes EMT and invasion in cancer cells", EMBO Reports 9, 582-589 (2008).
Cao, et al., "Individual microRNAs within the miR-17-92 Cluster Differentially Regulate Craniofacial Development", 92nd General Session & Exhibition of the IADR Africa/Middle East Regional Meeting, Cape Town, South Africa, Abstract, Apr. 2014.
Cao, et al., "MicroRNAs Play a Critical Role in Tooth Development", J Dent Res 89, 779-784 (2010).
Cao, et al., "Tbx1 regulates progenitor cell proliferation in the dental epithelium by modulating Pitx2 activation of p21", Dev Biol 347, 289-300 (2010).
Cao, et al., "The Pitx2:miR-200c/141:noggin pathway regulates Bmp signaling and ameloblast differentiation", Development 140(16), 3348-3359 (2013).
Chavez, et al., "Characterization of Dental Epithelial Stem Cells from the Mouse Incisor with Two-Dimensional and Three-Dimensional Platforms", Tissue Eng Part C Methods 19, 15-24 (2013).
Chavez, et al., "Isolation and culture of dental epithelial stem cells from the adult mouse incisor", J Vis Exp 87, e51266, 7 pages (2014).
Chen, et al., "Adhesion in the stem cell niche: biological roles and regulation", Development 140, 255-265 (2013).
Chen, et al., "Maintenance of Amelogenin Gene Expression by Transformed Epithelial Cells of Mouse Enamel Organ", Archs Oral Biol 37(10), 771-778 (1992).
Chu, et al., "WNT5A signaling affects pituitary gland shape", Mech Dev 121(2), 183-194 (2004).
Cox, et al., "Differential Regulation of Gene Expression by PITX2 Isoforms", J Biol Chem 277, 25001-25010 (2002).
Cui, et al., "Overexpression of Smad2 in Tgf-beta3-null mutant mice rescues cleft palate", Dev Biol 278, 193-202 (2005).
Cui, et al., "WNT signaling determines tumorigenicity and function of ESC-derived retinal progenitors", J Clin Invest 123, 1647-1661 (2013).
De Hoon, et al., "Open source clustering software", Bioinformatics 20, 1453-1454 (2004).
Denbesten, et al., "Characterization of human primary enamel organ epithelial cells in vitro", Arch Oral Biol 50, 689-694 (2005).
Farges, et al., "Morphological and immunocytochemical characterization of cultured rat incisor cervical epithelial cells", Arch Oral Biol. 36, 737-745 (1991).
Filali, et al., "Wnt-3A/beta-catenin signaling induces transcription from the LEF-1 promoter", J Biol Chem 277(36), 33398-33410 (2002).
Gat, et al., "De Novo hair follicle morphogenesis and hair tumors in mice expressing a truncated beta-catenin in skin", Cell 95, 605-614 (1998).
Gay, et al., "Differentiation of Human Dental Stem Cells Reveal a Role for microRNA-218", J Periodontal Res 49, 110-120 (2014).
Giardine, et al., "Galaxy: a platform for interactive large-scale genome analysis", Genome Res 15, 1451-1455 (2005).
Goecks, et al., "Galaxy: a comprehensive approach for supporting accessible, reproducible, and transparent computational research in the life sciences", Genome Biol 11, R86, 13 pages (2010).
Gregory, et al., "The miR-200 family and miR-205 regulate epithelial to mesenchymal transition by targeting ZEB1 and SIP1", Nature Cell Biol 10, 593-601 (2008).
Gronthos, et al., "A method to isolate and culture expand human dental pulp stem cells", Methods Mol Biol 698, 107-121 (2011).
Hanks, et al., "Dentin-specific proteins in MDPC-23 cell line", Eur J Oral Sci 106, 260-266 (1998).
Harada, et al., "FGF10 maintains stem cell compartment in developing mouse incisors", Development 129, 1533-1541 (2002).
Harada, et al., "Localization of Putative Stem Cells in Dental Epithelium and Their Association with Notch and Fgf Signaling", J Cell Biol 147, 105-120 (1999).
Harada, et al., "New perspectives on tooth development and the dental stem cell niche", Arch Histol Cytol 67, 1-11 (2004).
Hjalt, et al., "The Pitx2 protein in mouse development", Dev Dyn 218, 195-200 (2000).
Hogan, et al., "Morphogenesis", Cell 96, 225-233 (1999).
Hu, et al., "On the cutting edge of organ renewal: Identification, regulation, and evolution of incisor stem cells", Genesis 52, 79-92 (2014).
Hynes, et al., "Generation of Functional Mesenchymal Stem Cells from Different Induced Pluripotent Stem Cell Lines", Stem Cells Dev 23, 1084-1096 (2014).
Ikeda, et al., "Fully functional bioengineered tooth replacement as an organ replacement therapy", Proc Nat Acad Sci USA 106, 13475-13480 (2009).
Ivey, et al., "MicroRNAs as regulators of differentiation and cell fate decisions", Cell Stem Cell 7, 36-41 (2010).
Järvinen, et al., "Continuous tooth generation in mouse is induced by activated epithelial Wnt/β-catenin signaling", Proc Natl Acad Sci USA 103, 18627-18632 (2006).
Jernvall, et al., "Reiterative signaling and patterning during mammalian tooth morphogenesis", Mech Dev 92, 19-29 (2000).
Jheon, et al., "Expression of MicroRNAs in the Stem Cell Niche of the Adult Mouse Incisor", Plos ONE 6, e24536, 7 pages (2011).
Karpowicz, et al., "E-Cadherin Regulates Neural Stem Cell Self-Renewal", J Neurosci 29(12), 3885-3896 (2009).
Kawano, et al., "Characterization of Dental Epithelial Progenitor Cells Derived from Cervical-loop Epithelium in a Rat Lower Incisor", J Dent Res 83, 129-133 (2004).
Hendee, K , et al., "PITX2 deficiency and associated human disease: insights from the zebrafish model", Human Molecular Genetics 27(10), 1675-1695 (2018).
Ji, Y , et al., "Mutations in zebrafish pitx2 model congenital malformations in Axenfeld-Rieger syndrome but do not disrupt left-right placement of visceral organs", Dev Biol 416(1), 69-81 (2016).
Martinez, N J , et al., "MicroRNA gene regulatory pathways in the establishment and maintenance of ESC identity", Cell Stem Cell 7, 31-35 (2010).

* cited by examiner

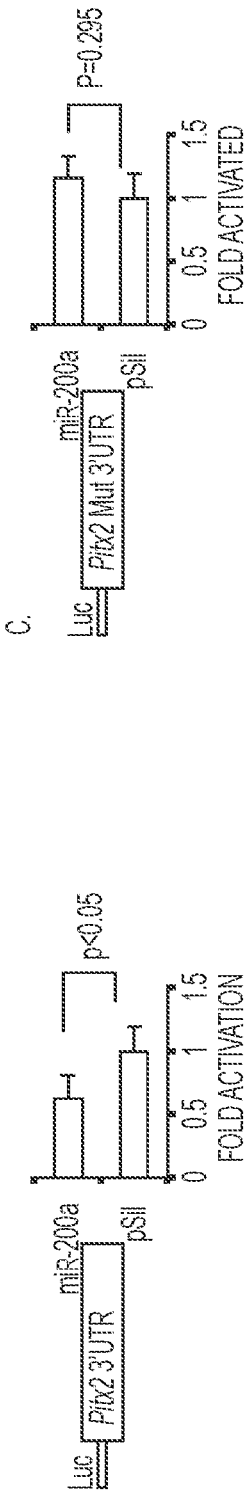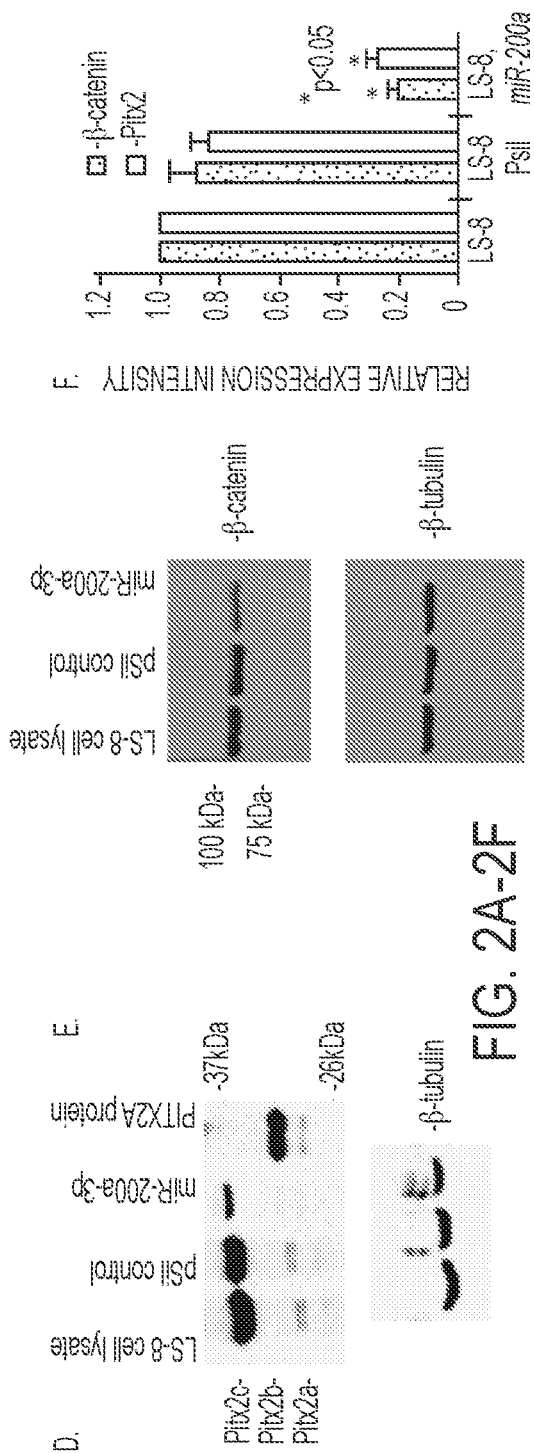
FIG. 2A-2F

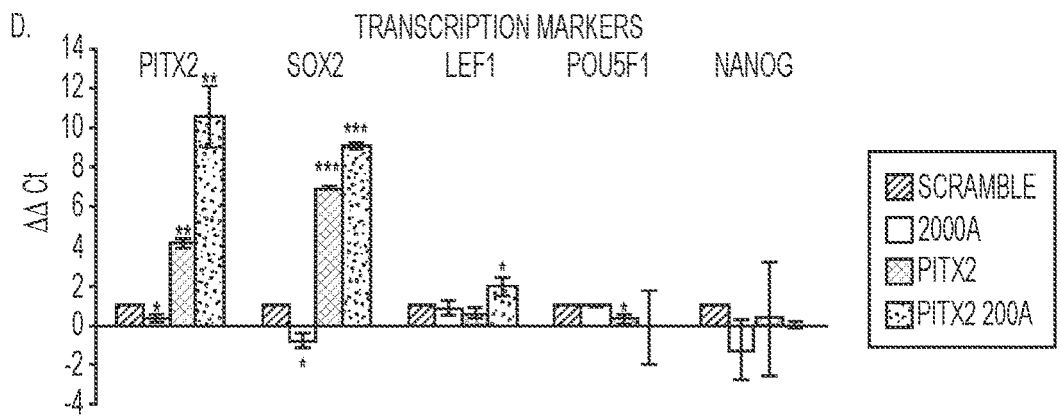
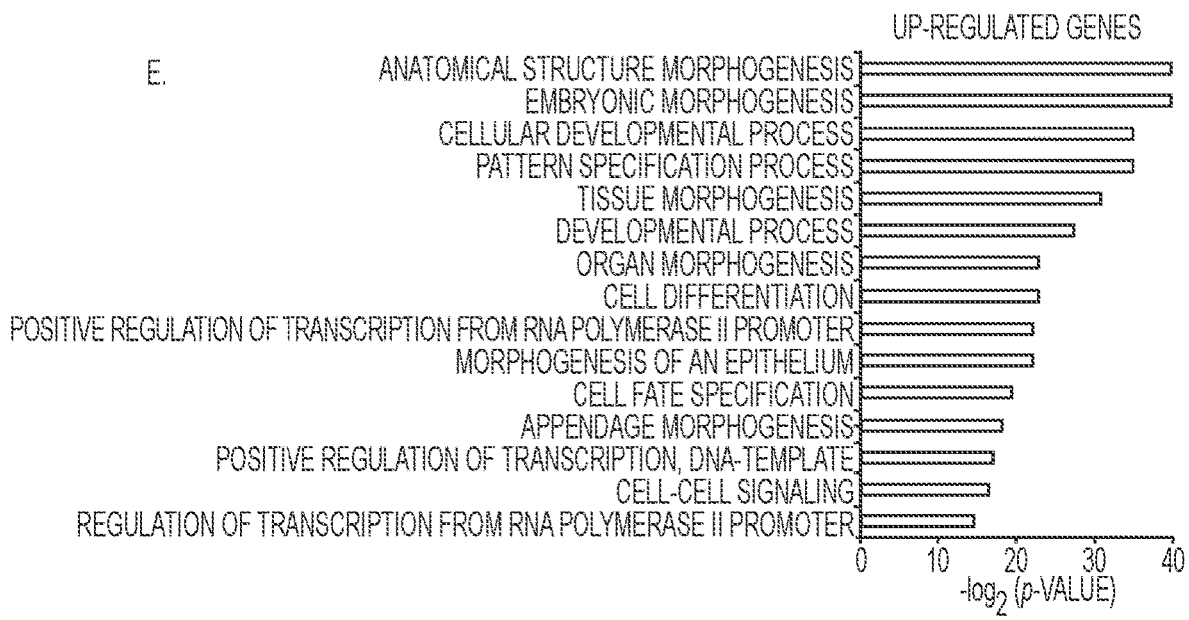
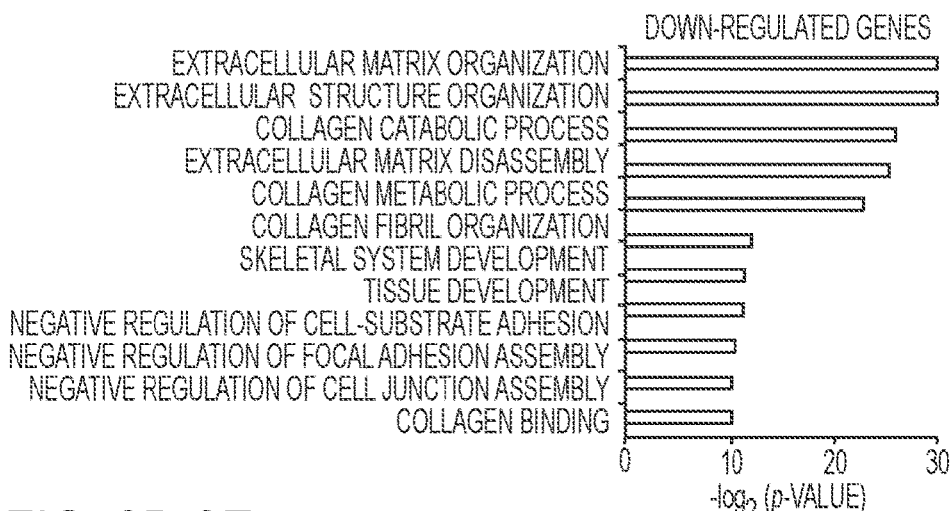
FIG. 9D-9E

TABLE 1: SELECTED MURINE DENTAL EPITHELIAL GENES IN P0 MOUSE DENTAL EPITHELIUM COMPARED TO MESENCHYME; CONVERTED ORAL EPITHELIAL (LS-8) CELLS COMPARED TO NON-TRANSFORMED ORAL EPITHELIAL (LS-8) CELLS AND CONVERTED DENTAL MESENCHYME (MDPC) CELLS COMPARED TO NON-TRANSFORMED DENTAL MESENCHYME (MDPC) CELLS.

| GENE | P0 DENTAL EPI. VS. | P0 DENTAL MES. | CONVERTED CELLS VS. ORAL EPI CELLS | CONVERTED CELLS VS. DENTAL MES CELLS |
|---|---|---|---|---|
| Tbx5 | HIGH EXP. | (-) 15-FOLD | (+) 2-FOLD OR LESS | (+) 4.1-FOLD |
| Satb1 | MED EXP. | (-) 2-FOLD | (+) 2-FOLD OR LESS | (+) 10-FOLD |
| Pitx1 | HIGH EXP. | (-) 7-FOLD | (+) 2-FOLD OR LESS | (+) 18-FOLD |
| Lhx6 | MED EXP. | (-) 8.5-FOLD | (+) 2-FOLD OR LESS | (+) 2.1-FOLD |
| Isl1 | HIGH EXP. | (-) 6.3-FOLD | (+) 2-FOLD OR LESS | (+) 10.4-FOLD |
| Dach1 | MED EXP. | (-) 2.7-FOLD | (+) 2-FOLD OR LESS | (+) 7.9-FOLD |
| Aff2 | MED EXP. | (-) 4.1-FOLD | (+) 2-FOLD OR LESS | (+) 2.8-FOLD |
| Lef1 | MED EXP. | (-) 2.4-FOLD | (+) 2-FOLD OR LESS | (+) 15.4-FOLD |
| Hmx1 | LOW EXP. | (-) 3.2-FOLD | (+) 2-FOLD OR LESS | (+) 10.8-FOLD |
| Tbx1 | HIGH EXP. | (-) 5.5-FOLD | (+) 2-FOLD OR LESS | (+) 2-FOLD OR LESS |
| Foxj3 | HIGH EXP. | (-) 10-FOLD | (+) 2-FOLD OR LESS | (+) 6.2-FOLD OR LESS |
| Irf6 | HIGH EXP. | (-) 7-FOLD | (+) 1.4-FOLD | (+) 2-FOLD OR LESS |
| Cacna1g | HIGH EXP. | (-) 9-FOLD | (+) 2.3-FOLD | (+) 2-FOLD OR LESS |
| Gadd45a | HIGH EXP. | (-) 2.6-FOLD | (+) 2-FOLD OR LESS | (+) 2-FOLD OR LESS |
| Mmp20 | LOW HIGH | (-) 1.6-FOLD | (+) 2-FOLD OR LESS | (+) 2.1-FOLD OR LESS |
| Enam | HIGH EXP. | (-) 11-FOLD | (+) 2-FOLD OR LESS | (+) 2-FOLD OR LESS |

FIG. 12

SEQUENCE LISTING

```
<160> NUMBER OF SEQ ID NOS: 25

<210> SEQ ID NO 1
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
uaacacuguc ugguaacgau gu                                             22

<210> SEQ ID NO 2
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
uaacacuguc ugguaaagau gg                                             22

<210> SEQ ID NO 3
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
uaauacugcc ugguaaugau ga                                             22

<210> SEQ ID NO 4
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
uaauacugcc ggguaaugau gga                                            23

<210> SEQ ID NO 5
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
uaauacuguc ugguaaaacc gu                                             22
```

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ttcttggctc tgtatgggag a                                              21

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cccctcttgc cttttcag                                                  19

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aggcaacaga cacctgcact                                                20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gaatgactgt ctcccctcca                                                20

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gcagctatca accagatcc                                                 19

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gatgtaggca gctgtcattc                                                20

-continued

```
<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gcttcagttc cgaggtctac                                                    20

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
agatgccgct tcacttgtga t                                                  21

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gagctgctgg ccaagatcac                                                    20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gacttggatc cggcgttatg                                                    20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
agtgactcgc aatgatgtgg                                                    20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gaaccgcttc cttcatagtc                                                    20

<210> SEQ ID NO 18
```

```
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
catcactgcc acccagaag                                                    19

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cagtgagctt cccgttcag                                                    19

<210> SEQ ID NO 20
<211> LENGTH: 45
<212> TYPE: RNA
<213> ORGANISM: Mus sp.

<400> SEQUENCE: 20
uuugcaguaa cuguuaguuu uuaaguagug uuauguucua gugaa                       45

<210> SEQ ID NO 21
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
uguagcaaug gucugucaca au                                                22

<210> SEQ ID NO 22
<211> LENGTH: 46
<212> TYPE: RNA
<213> ORGANISM: Homo sapiens

<400> SEQUENCE: 22
aaaagcaguu guuaguaaua ucacaacagu guuuuaaag guuagg                       46

<210> SEQ ID NO 23
<211> LENGTH: 46
<212> TYPE: RNA
<213> ORGANISM: Mus sp.

<400> SEQUENCE: 23
aaaagcaguu guuaguacua ucacgacagu guuuuaaag gcuagg                       46

<210> SEQ ID NO 24
<211> LENGTH: 46
<212> TYPE: RNA
<213> ORGANISM: Rattus sp.

<400> SEQUENCE: 24
aaaagcaguu guuaguacuc ucacgacagu guuuuaaag gcuagg                       46

<210> SEQ ID NO 25
```

```
<211> LENGTH: 46
<212> TYPE: RNA
<213> ORGANISM: Canis sp.

<400> SEQUENCE: 25
aaaagcaguu guuaguacuc ucacaacagu guuuuuaaag guuagg            46
```

METHODS TO GENERATE EPITHELIAL CELLS

RELATED APPLICATION

This application claims the benefit of priority of U.S. Provisional Application Ser. No. 62/079,260 filed on Nov. 13, 2014, which application is herein incorporated by reference.

GOVERNMENT FUNDING

This invention was made with government support under DE13941 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Sep. 28, 2015, is named 17023_152WO1_SL.txt and is 5,553 bytes in size.

BACKGROUND OF THE INVENTION

Dentists have been fixing cavities with metal fillings since the nineteenth century, but these metal compositions are less than optimal because they possess very different in physical characteristics from the original tooth composition. The outer covering of an intact tooth is enamel, which is the hardest substance in the human body and contains the highest percentage of minerals. The body makes enamel by growing tiny mineral crystals in a highly regular crystal lattice. Underneath this ceramic-like covering is dentin, which is like hard clay reinforced by fibers of collagen. Enamel and dentin are remarkably strong and long-lasting, and they can repair themselves.

Current studies attempt to repair or recreate new teeth using dental stem cells and isolated dental epithelial-mesenchyme interactions to generate epithelial cells and tissue for tooth bioengineering and regeneration. Many of the genes required for epithelial cell proliferation and differentiation during tooth organogenesis and regeneration have been identified and are being used in research to make teeth. A common theme in recent studies relies on the isolation of dental progenitor or stem cells to generate competent differentiated dental epithelial cells. These procedures are intrusive and provide limited amounts of material. Difficulties exist, however, with isolating and utilizing a sufficient quantity of adult stem cells that can be used therapeutically, and ethical issues exist with the use of embryonic stem cells.

Currently there is a need for inducing tooth regeneration to repair decayed or destroyed teeth instead of using metal or ceramic fillings used conventionally, and instead of using adult or embryonic stem cells.

SUMMARY OF THE INVENTION

Accordingly the invention provides in certain embodiments, a method of generating a re-programmed differentiated epithelial cell comprising (a) contacting a non-stem somatic cell obtained from a subject with an effective amount of a de-differentiation agent to form a de-differentiated cell, and (b) transfecting the de-differentiated cell with an expression cassette comprising a promoter operably linked to a nucleic acid encoding a conversion agent to form a re-programmed differentiated cell. In certain embodiments, the present invention further comprises (c) growing the re-programmed differentiated cell on a mesh in order to form a multi-cellular tissue. In certain embodiments, the present invention further comprises (d) implanting the multi-cellular tissue into the subject.

The invention provides in certain embodiments, a method of generating a re-programmed differentiated epithelial cell comprising (a) contacting a non-stem somatic cell obtained from a subject with an effective amount of a de-differentiation agent to form a de-differentiated cell, and (b) contacting the de-differentiated cell with a conversion agent to form a re-programmed differentiated cell. The cells must take up the conversion agent in order for them to be reprogrammed and converted. In certain embodiments, the conversion agent is complexed with a transfection reagent, nanoparticle, calcium reagent or lipid. In certain embodiments, the conversion agent enters the cell directly without a conversion agent. In certain embodiments, the present invention further comprises (c) growing the re-programmed differentiated cell on a mesh in order to form a multi-cellular tissue. In certain embodiments, the present invention further comprises (d) implanting the multi-cellular tissue into the subject.

The invention provides in certain embodiments, a method of generating an epithelial cell comprising contacting an odontoblast mesenchyme cell or an oral epithelial cell obtained from a subject with an effective amount of 1) Pitx2; and 2) miR-200a-3p to generate a dental epithelial cell, wherein the dental epithelial cell expresses amelogenin.

The invention provides in certain embodiments, a cell produced by a method described above.

The invention provides in certain embodiments, a method of repair or re-generation of tissue in vivo comprising administering a cell produced by a method described above to a subject in need thereof.

BRIEF DESCRIPTION OF THE FIGURES

FIGS. 2A-2F. miR-200a-3p directly targets the Pitx2 and β-catenin 3'-UTR and represses Pitx2 and β-catenin expression. A) miR-200a-3p is evolutionarily conserved among several vertebrate species and the miR-200a target sites in the Pitx2 and β-catenin 3'-UTR are shown (SEQ ID NOS 20-25, respectively, in order of appearance). B) Pitx2 3'UTR luciferase construct transfected with either miR-200a or empty vector in LS-8 cells. Luciferase activity was measured using the dual luciferase system to control for transfection efficiency and normalization. N=3, p<0.05. C) As a control the miR-200a target site was mutated in the Pitx2 3'UTR and showed no inhibition when co-transfected with miR-200a or empty vector, N=3, p=0.295. D) miR-200a-3p represses endogenous Pitx2a and Pitx2c isoform expression. Western blot of endogenous Pitx2 in miR-200a precursor transfected LS-8 cells 48 h post-transfection. β-tubulin is shown as a loading control. The Pitx2b isoform was not detected in LS-8 cells. E) miR-200a represses endogenous β-catenin expression. Western blot of β-catenin protein in control or miR-200a precursor transfected LS-8 cells 48 h post-transfection. β-tubulin is shown as a loading control. LS-8 cell lysate (empty vector, Mock) and pSil-neg vector served as controls. F) Quantitation of β-catenin and Pitx2 endogenous expression from three Western blots using different LS-8 cell lysates expressing miR-200a or controls (empty vector or no vector; N=3; *p<0.05).

FIGS. 9A-9E. Reprogrammed MDPC odontoblast cells express amelogenin and dental epithelial factors. A) MDPC mesenchymal cells are transduced with Pitx2 and a combination of Pitx2 and miR-200a or lentiviral vector expressing a scrambled RNA control. Cells were FACS sorted and GFP and immunofluorescence microscopy analysis of changes in the expression levels of Cdh1 and Amelx were observed after eight weeks. Pitx2 transduced cells express low levels of E-cadherin (Cdh1) and amelogenin (Amelx). Pitx2 and miR-200a transduced cells express both Cdh1 and Amelx and form tight junctions between cells. GFP expression shows the cells were transduced with the lentiviral vector. B) RNA-seq analysis of gene expression in response to Pitx2-miR-200a overexpression in MDPC cells. Significantly up- and down regulated genes that have at least 2 fold of expression level change were labeled red and blue, respectively. All expression levels were estimated by FPKM. C)

Heat map showing the expression dynamics of selected EMT genes upon Pitx2-miR-200a overexpression. Epithelial specific and mesenchymal specific genes were hierarchically clustered, respectively. D) Real time PCR of selected transcription factors associated with dental epithelial proliferation and differentiation. Endogenous Sox2, and Lef-1 were increased in the Pitx2-miR-200a transduced LS-8 cells. Pitx2 was over expressed as expected (Pitx2 cDNA is not regulated by miR-200a). Pou5fl (Oct4) and Nanog were not significantly changed. N>3, *p<0.05, **p<0.01. E) Gene Ontology (GO) analysis significantly up- and down-regulated genes. Top enriched GO terms (−log 2 p value>10) are highlighted for both up-regulated (red) and down-regulated (blue) genes that are related to EMT and morphogenic functions.

Figures 10A, 10B:
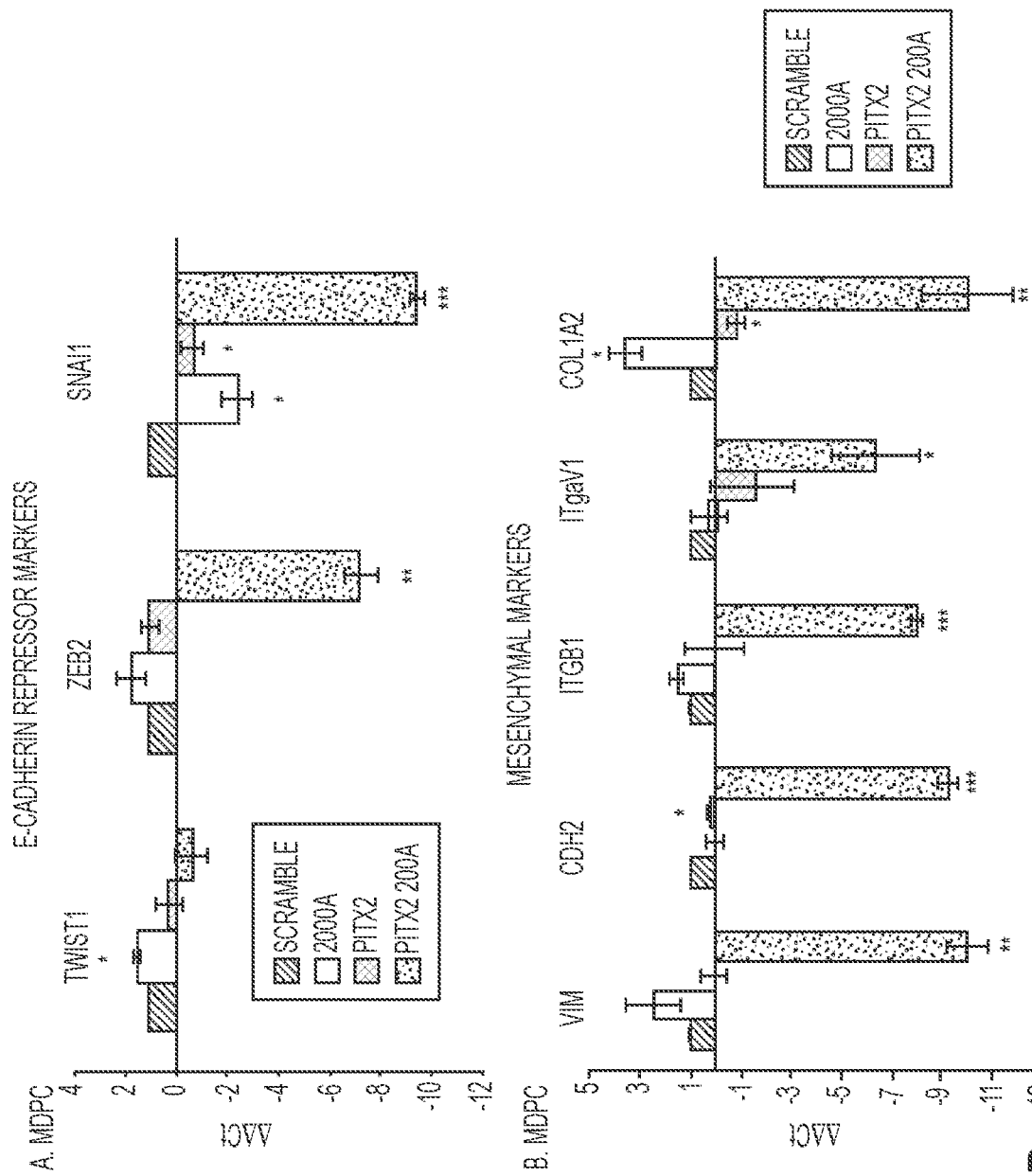

FIGS. 10A-10B. FACS sorted transduced MDPC cells were analyzed for specific gene expression. A) The E-cadherin repressor genes Zeb2 and Snail1 were significantly decreased in Pitx2-miR-200a transduced cells compared to scrambled control. N=3. B) All measured mesenchymal markers were significantly down regulated in Pitx2-miR-200a transduced cells compared to scrambled control. N=3.

Figure 11:
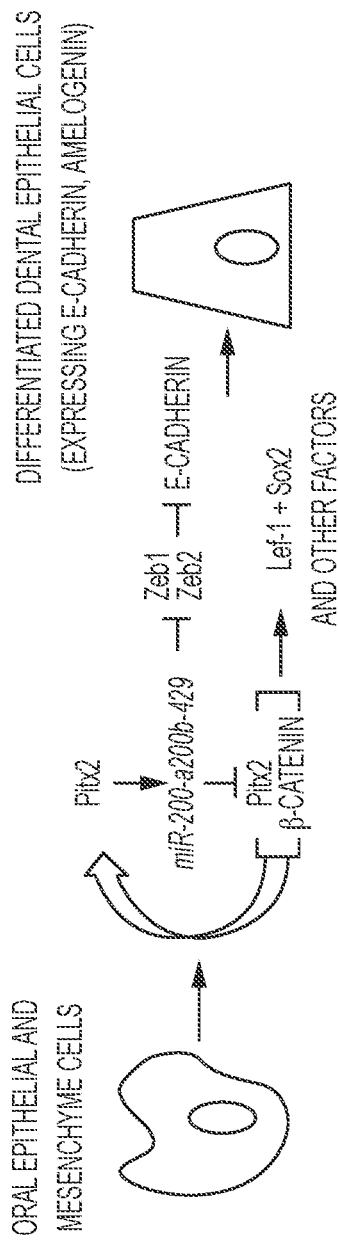

FIG. 11. Model for the role of Pitx2 and miR-200a in cell conversion. To convert oral epithelial or dental mesenchyme cells to differentiated dental epithelium, cells are transfected with Pitx2, which regulates endogenous miR-200a expression. It has been shown that miR-200a inhibits Zeb1 and Zeb2, which repress E-cadherin expression. miR-200a feeds back to also repress Pitx2 and β-catenin expression. Pitx2 activates its own expression in concert with β-catenin providing a constant feed-back loop to fine tune both Pitx2 and miR-200a expression. However, over expression of Pitx2 cDNA drives Lef-1 and other dental epithelial factors and promotes dental epithelial cell conversion with miR-200a over-expression.

FIG. 12 Selected murine P0 dental epithelial markers were identified by RNA-seq and DNA microarrays and compared to dental mesenchyme gene expression. RNA-seq. experiments identified gene expression changes of the epithelial cell markers in converted oral epithelial cells and dental mesenchyme cells.

DETAILED DESCRIPTION

The present technology is a method that uses easily accessible oral epithelial cells, which are re-programmed to create cells with stem cell-like features and then are converted into dental epithelial cells. The first step in the process is a de-differentiation step (e.g., initiated by the introduction of Pitx2) of isolated oral epithelial cells in culture. Subsequently, a conversion agent (e.g., miR-200a) is transfected to create dental epithelial cells, which can be used for tooth regeneration procedures in the clinic. This methodology allows a patient to utilize his or her own cells for the regeneration procedure.

In certain embodiments, the present invention provides a method of generating a re-programmed differentiated epithelial cell comprising (a) contacting a non-stem somatic cell obtained from a subject with an effective amount of a de-differentiation agent to form a de-differentiated cell, and (b) transfecting the de-differentiated cell with an expression cassette comprising a promoter operably linked to a nucleic acid encoding a conversion agent to form a re-programmed differentiated cell.

In certain embodiments, the promoter is a polII or polIII promoter. In certain embodiments, the polIII promoter is a U6, H1, H3, or H4 promoter. In certain embodiments, the promoter is a polII promoter. In certain embodiments, the promoter is a tissue-specific promoter. In certain embodiments, the promoter is an inducible promoter.

In certain embodiments, the expression cassette further comprises a marker gene.

In certain embodiments, the expression cassette is contained in a vector. In certain embodiments, the vector is a viral vector. In certain embodiments, the vector is an adeno-associated virus (AAV) vector. In certain embodiments, the vector is modified such that is enters specific cells and expresses the gene or miR.

In certain embodiments, the present invention provides a method of generating a re-programmed differentiated epithelial cell comprising (a) contacting a non-stem somatic cell obtained from a subject with an effective amount of a de-differentiation agent to form a de-differentiated cell, and (b) contacting the de-differentiated cell with a conversion agent to form a re-programmed differentiated cell. In certain embodiments, the conversion agent is complexed with a transfection reagent, nanoparticle, calcium reagent or lipid.

In certain embodiments, the invention further comprises (c) growing the re-programmed differentiated cell on a mesh in order to form a multi-cellular tissue. In certain embodiments, the mesh comprises collagen (e.g., collagen gel or collagen fibers), matrix, sponge, nanoparticle mesh or scaffold, lipids, or fibers (e.g., nanofibers). In certain embodiments, the growing is for 2 to 10 weeks. In certain embodiments, the growing is for 7 to 9 weeks.

In certain embodiments, the invention further comprises (d) implanting the multi-cellular tissue into the subject.

In certain embodiments, the non-stem somatic cell is an oral, ocular, pituitary, heart, liver, or pancreas cell. In certain embodiments, the non-stem somatic cell is a labial epithelial cell, and the differentiated cell is an ameloblast. In certain embodiments, the non-stem somatic cell is a mesenchymal cell, and the differentiated cell is an odontoblast. In certain embodiments, the non-stem somatic cell is an oral epithelial cell and/or odontoblast mesenchyme cell and the re-programmed cell is a dental epithelial cell. In certain embodiments, the dental epithelial cell is an amelogenin-producing dental epithelial cell.

In certain embodiments, the present invention provides a method of generating an epithelial cell comprising contacting an odontoblast mesenchyme cell or an oral epithelial cell obtained from a subject with an effective amount of 1) Pitx2; and 2) miR-200a-3p to generate a dental epithelial cell, wherein the dental epithelial cell expresses amelogenin. In certain embodiments, the miR-200a-3p represses Pitx2 and β-catenin expression.

In certain embodiments, the present invention provides a cell produced by a method described above.

In certain embodiments, the present invention provides a method of repair or re-generation of tissue in vivo comprising administering a cell produced by a method described above.

De-Differentiation Agents

In certain embodiments, the de-differentiation agent is an anti-miR or miR inhibitor, is a transcription factor or is an agent that causes over-expression of a miR. In certain embodiments, the he non-stem somatic cell is bone, and the de-differentiation agent is an anti-miR or inhibitors of miR-200c, miR-200b, miR-141, miR-429, miR-146, miR-34, miR-17-92, miR-218, miR-29b, miR-222, miR-148, miR-31, miR-136, miR-210, miR-335, miR-99 and/or miR-3960; and/or is transcription factor Runx2, BMP, and/or Msx; and/or causes over-expression of miR-200a.

In certain embodiments, the non-stem somatic cell is cartilage, and the de-differentiation agent is an anti-miR or inhibitors of miR-200c, miR-200b, miR-141, miR-140, and/or miR-429; and/or is transcription factor Sox9, Wnts, and/or FoxO3; and/or causes over-expression of miR-146, miR-148, miR-34, miR-17-92, miR-218, miR-29b, miR-222, miR-148, miR-31, miR-136, miR-210, miR-335, miR-99, miR-3960, miR-146, 205, miR-33, miR-302, miR-145, miR-29, miR-221, miR-449, and/or miR-675.

In certain embodiments, the de-differentiation agent is Pitx2. Pitx2 acts as a transcription factor and regulates pro-collagen lysyl hydroxylase gene expression. This protein is involved in the development of the eye, tooth and abdominal organs. There have been studies showing different isoforms of the transcription factor: Pitx2a, Pitx2b, and Pitx2c, each with distinct and non-overlapping functions.

Conversion Agents

In certain embodiments, the conversion agent is agent is miR-200a, miR-200b, miaR-200c, miR-141, miR-429, miR-23, miR-24, miR-27, miR-17-92, miR-218, miR-96, Pitx2, Tbx1, Sox2, beta-catenin, Foxj3, and/or Sonic HedgeHog, and the re-programmed differentiated cell is a dental, tooth, or palate cell.

In certain embodiments, the conversion agent is agent is miR-200a, miR-200b, miR-200c, miR-141, miR-429, miR-203, miR-205, miR-23, miR-27, miR-24, miR-96, miR-146, miR-26, Tbx1, Pitx2, Lef-1, and/or beta-catenin and the re-programmed differentiated cell is a skin cell.

In certain embodiments, the conversion agent up-regulates stem cell marker Sox2 and at least one proliferation gene. In certain embodiments, the conversion agent down-regulates decreased expression of mesenchymal markers. In certain embodiments, the conversion agent increases E-cadherin expression and ameloblast-specific factors. In certain embodiments, the conversion agent is miR-200a-3p.

miRs

MicroRNAs (miRNAs) are small, non-coding RNA molecules, which are able to regulate gene expression posttranscriptionally through degradation of the messenger RNA or inhibition of translation. The total number of different miRNAs is estimated to be approximately 1000-1500. miRNAs thus constitute approximately 1% of the human genome. miRNAs have been discovered in various species and appear to be highly conserved.

Although the target genes (or targets) and thus the biological functions of miRNAs have to date largely not been able to be identified, it is estimated that miRNAs regulate up to 30% of the genes of the human genome.

Firstly, miRNA genes are transcribed by RNA polymerase II into long primary miRNAs (pri-miRNAs). The further processing of these pri-miRNAs takes place in a step-by-step manner and in various compartments. Pri-miRNAs are firstly transformed in the cell nucleus by the RNase III enzyme *Drosha* into precursor miRNAs (pre-miRNAs) comprising approximately 70-80 nucleotides. *Drosha* forms a microprocessor complex with the RNA-binding protein DGCR8. Pre-miRNA hairpins are conveyed out of the cell nucleus by the protein exportin-5 and Ran-GTP as cofactor. In the cytoplasm, the pre-miRNA is processed by the RNase II enzyme Dicer to form duplex-miRNAs comprising approximately 22 nucleotides. Dicer interacts in this case with the double-stranded RNA-binding protein TRBP. The miRNA duplex molecules are then unwound, so that mature miRNA is obtained. This mature miRNA is then incorporated in a ribonucleoprotein complex (miRNP), which is very similar to the RNA-induced silencing complex (RISC), the effector molecule of interfering RNA (RNAi) (Hutvagner and Zamore, 2002).

In this form, miRNAs can lead to a downregulation of the respective target gene via two different mechanisms: a) translational inhibition or b) target mRNA cleavage. The choice of mechanism depends on the degree of complementarity between miRNA and the target gene in combination with a so-called *Argonaute* Protein (Meister et al., 2005). In the case of almost perfect complementarity, a cleavage of the target gene takes place with subsequent RNA degradation, whereas a translational inhibition takes place in the case of only partial complementarity (Hutvagner and Zamore, 2002).

miRs have been identified as key regulators of progenitor cell differentiation and modulators of cell fate decisions. miRs regulate the fate of stem cells in many different tissues and organs through the specification or differentiation of cell types. miRs can target cell cycle regulators, promote differentiation by inactivating transcriptional repressors, integrate with transcriptional and signaling networks in bone formation, muscle differentiation, neurogenesis, and tooth and craniofacial morphogenesis. The use of miRs in cell reprogramming is a new field of research that has great promise for tooth regeneration.

miR-200 is primarily associated with increased migration/invasion and metastatic activity of various cancer types.

| | |
|---|---|
| mmu-miR-200a-3p | UAA<u>CA</u>CUGUCUGGUAACGAUGU (SEQ ID NO: 1) |
| mmu-miR-141-3p | UAA<u>CA</u>CUGUCUGGUAAAGAUGG (SEQ ID NO: 2) |
| mmu-miR-200b-3p | UAA<u>UA</u>CUGCCUGGUAAUGAUGA (SEQ ID NO: 3) |
| mmu-miR-200c-3p | UAA<u>UA</u>CUGCCGGGUAAUGAUGGA (SEQ ID NO: 4) |
| mmu-miR-429-3p | UAA<u>UA</u>CUGUCUGGUAAAACCGU (SEQ ID NO: 5) |

Vectors and Expression Cassettes

A "vector" is defined to include, inter alia, any viral vector, as well as any plasmid, cosmid, phage or binary vector in double or single stranded linear or circular form that may or may not be self-transmissible or mobilizable, and that can transform prokaryotic or eukaryotic host either by integration into the cellular genome or exist extrachromosomally (e.g., autonomous replicating plasmid with an origin of replication).

"Expression cassette" as used herein means a nucleic acid sequence capable of directing expression of a particular nucleotide sequence in an appropriate host cell, which may include a promoter operably linked to the nucleotide sequence of interest that may be operably linked to termination signals. The coding region usually codes for a functional RNA of interest, for example an miRNA. The expression cassette including the nucleotide sequence of interest may be chimeric. The expression cassette may also be one that is naturally occurring but has been obtained in a recombinant form useful for heterologous expression. The expression of the nucleotide sequence in the expression cassette may be under the control of a constitutive promoter or of a regulatable promoter that initiates transcription only when the host cell is exposed to some particular stimulus. In the case of a multicellular organism, the promoter can also be specific to a particular tissue or organ or stage of development.

Such expression cassettes can include a transcriptional initiation region linked to a nucleotide sequence of interest. Such an expression cassette is provided with a plurality of restriction sites for insertion of the gene of interest to be under the transcriptional regulation of the regulatory regions. The expression cassette may additionally contain selectable marker genes.

"Coding sequence" refers to a DNA or RNA sequence that codes for a specific amino acid sequence. It may constitute an "uninterrupted coding sequence," i.e., lacking an intron, such as in a cDNA, or it may include one or more introns bounded by appropriate splice junctions. An "intron" is a sequence of RNA that is contained in the primary transcript but is removed through cleavage and re-ligation of the RNA within the cell to create the mature mRNA that can be translated into a protein.

The term "RNA transcript" or "transcript" refers to the product resulting from RNA polymerase catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA" (mRNA) refers to the RNA that is without introns and that can be translated into protein by the cell.

"Regulatory sequences" are nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences that may be a combination of synthetic and natural sequences. As is noted herein, the term "suitable regulatory sequences" is not limited to promoters. However, some suitable regulatory sequences useful in the present invention will include, but are not limited to constitutive promoters, tissue-specific promoters, development-specific promoters, regulatable promoters and viral promoters.

"5' non-coding sequence" refers to a nucleotide sequence located 5' (upstream) to the coding sequence. It is present in the fully processed mRNA upstream of the initiation codon and may affect processing of the primary transcript to mRNA, mRNA stability or translation efficiency.

"3' non-coding sequence" refers to nucleotide sequences located 3' (downstream) to a coding sequence and may include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor.

The term "translation leader sequence" refers to that DNA sequence portion of a gene between the promoter and coding sequence that is transcribed into RNA and is present in the fully processed mRNA upstream (5') of the translation start codon. The translation leader sequence may affect processing of the primary transcript to mRNA, mRNA stability or translation efficiency.

"Promoter" refers to a nucleotide sequence, usually upstream (5') to its coding sequence, which directs and/or controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions. Examples of promoters that may be used in the present invention include the mouse U6 RNA promoters, synthetic human H1 RNA promoters, SV40, CMV, RSV, RNA polymerase II and RNA polymerase III promoters.

The "initiation site" is the position surrounding the first nucleotide that is part of the transcribed sequence, which is also defined as position +1. With respect to this site all other sequences of the gene and its controlling regions are numbered. Downstream sequences (i.e., further protein encoding sequences in the 3' direction) are denominated positive, while upstream sequences (mostly of the controlling regions in the 5' direction) are denominated negative.

Promoter elements, particularly a TATA element, that are inactive or that have greatly reduced promoter activity in the absence of upstream activation are referred to as "minimal or core promoters." In the presence of a suitable transcription factor, the minimal promoter functions to permit transcription. A "minimal or core promoter" thus consists only of all basal elements needed for transcription initiation, e.g., a TATA box and/or an initiator.

"Constitutive expression" refers to expression using a constitutive or regulated promoter. "Conditional" and "regulated expression" refer to expression controlled by a regulated promoter.

"Operably-linked" refers to the association of nucleic acid sequences on single nucleic acid fragment so that the function of one of the sequences is affected by another. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

"Expression" refers to the transcription and/or translation of an endogenous gene, heterologous gene or nucleic acid segment, or a transgene in cells. For example, in the case of siRNA constructs, expression may refer to the transcription of the siRNA only. In addition, expression refers to the transcription and stable accumulation of sense (mRNA) or functional RNA. Expression may also refer to the production of protein.

"Altered levels" refers to the level of expression in transgenic cells or organisms that differs from that of normal or untransformed cells or organisms.

"Overexpression" refers to the level of expression in transgenic cells or organisms that exceeds levels of expression in normal or untransformed cells or organisms.

"Antisense inhibition" refers to the production of antisense RNA transcripts capable of suppressing the expression of protein from an endogenous gene or a transgene.

"Transcription stop fragment" refers to nucleotide sequences that contain one or more regulatory signals, such as polyadenylation signal sequences, capable of terminating transcription. Examples include the 3' non-regulatory regions of genes encoding nopaline synthase and the small subunit of ribulose bisphosphate carboxylase.

"Translation stop fragment" refers to nucleotide sequences that contain one or more regulatory signals, such as one or more termination codons in all three frames, capable of terminating translation. Insertion of a translation stop fragment adjacent to or near the initiation codon at the 5' end of the coding sequence will result in no translation or improper translation. Excision of the translation stop fragment by site-specific recombination will leave a site-specific sequence in the coding sequence that does not interfere with proper translation using the initiation codon.

The terms "cis-acting sequence" and "cis-acting element" refer to DNA or RNA sequences whose functions require them to be on the same molecule. An example of a cis-acting sequence on the replicon is the viral replication origin.

The terms "trans-acting sequence" and "trans-acting element" refer to DNA or RNA sequences whose function does not require them to be on the same molecule.

"Chromosomally-integrated" refers to the integration of a foreign gene or nucleic acid construct into the host DNA by covalent bonds. Where genes are not "chromosomally integrated" they may be "transiently expressed." Transient expression of a gene refers to the expression of a gene that is not integrated into the host chromosome but functions independently, either as part of an autonomously replicating plasmid or expression cassette, for example, or as part of another biological system such as a virus.

The following terms are used to describe the sequence relationships between two or more nucleic acids or polynucleotides: (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well-known in the art. Thus, the determination of percent identity between any two sequences can be accomplished using a mathematical algorithm.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST (in BLAST 2.0) can be utilized. Alternatively, PSI-BLAST (in BLAST 2.0) can be used to perform an iterated search that detects distant relationships between molecules. When utilizing BLAST, Gapped BLAST, PSI-BLAST, the default parameters of the respective programs (e.g. BLASTN for nucleotide sequences) can be used. The BLASTN program (for nucleotide sequences) uses as defaults a wordlength (W) of 11, an expectation (E) of 10, a cutoff of 100, M=5, N=−4, and a comparison of both strands. Alignment may also be performed manually by inspection.

For purposes of the present invention, comparison of nucleotide sequences for determination of percent sequence identity to the promoter sequences disclosed herein is preferably made using the BlastN program (version 1.4.7 or later) with its default parameters or any equivalent program.

By "equivalent program" is intended any sequence comparison program that, for any two sequences in question, generates an alignment having identical nucleotide matches and an identical percent sequence identity when compared to the corresponding alignment generated by the preferred program.

(c) As used herein, "sequence identity" or "identity" in the context of two nucleic acid sequences makes reference to a specified percentage of nucleotides in the two sequences that are the same when aligned for maximum correspondence over a specified comparison window, as measured by sequence comparison algorithms or by visual inspection.

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e) The term "substantial identity" of polynucleotide sequences means that a polynucleotide comprises a sequence that has at least 70%, 71%, 72%, 73%, 74%, 75%, 76%, 77%, 78%, or 79%, preferably at least 80%, 81%, 82%, 83%, 84%, 85%, 86%, 87%, 88%, or 89%, more preferably at least 90%, 91%, 92%, 93%, or 94%, and most preferably at least 95%, 96%, 97%, 98%, or 99% sequence identity, compared to a reference sequence using one of the alignment programs described using standard parameters.

Another indication that nucleotide sequences are substantially identical is if two molecules hybridize to each other under stringent conditions. Generally, stringent conditions are selected to be about 5° C. lower than the thermal melting point (Tm) for the specific sequence at a defined ionic strength and pH. However, stringent conditions encompass temperatures in the range of about 1° C. to about 20° C., depending upon the desired degree of stringency as otherwise qualified herein.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted herein, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The Tm is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the Tm can be approximated from the equation: Tm 81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. Tm is reduced by about 1° C. for each 1% of mismatching; thus, Tm, hybridization, and/or wash conditions can be adjusted to hybridize to sequences of the desired identity. For example, if sequences with >90% identity are sought, the Tm can be decreased 10° C. Generally, stringent conditions are selected to be about 5° C. lower than the thermal melting point (Tm) for the specific sequence and its complement at a defined ionic strength and pH. However, severely stringent conditions can utilize a hybridization and/or wash at 1, 2, 3, or 4° C. lower than the thermal melting point (Tm); moderately stringent conditions can utilize a hybridization and/or wash at 6, 7, 8, 9, or 10° C. lower than the thermal melting point (Tm); low stringency conditions can utilize a hybridization and/or wash at 11, 12, 13, 14, 15, or 20° C. lower than the thermal melting point (Tm). Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), it is preferred to increase the SSC concentration so that a higher temperature can be used. Generally, highly stringent hybridization and wash conditions are selected to be about 5° C. lower than the thermal melting point (Tm) for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes (see, Sambrook and Russell 2001, for a description of SSC buffer). Often, a high stringency wash is preceded by a low stringency wash to remove background probe signal. For short nucleic acid sequences (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. Stringent conditions may also be achieved with the addition of destabilizing agents such as formamide. In general, a signal to noise ratio of 2× (or higher) than that observed for an unrelated probe in the particular hybridization assay indicates detection of a specific hybridization. Very stringent conditions are selected to be equal to the Tm for a particular nucleic acid molecule.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

The term "transformation" refers to the transfer of a nucleic acid fragment into the genome of a host cell, resulting in genetically stable inheritance. A "host cell" is a cell that has been transformed, or is capable of transformation, by an exogenous nucleic acid molecule. Host cells containing the transformed nucleic acid fragments are referred to as "transgenic" cells.

"Transformed," "transduced," "transgenic" and "recombinant" refer to a host cell into which a heterologous nucleic acid molecule has been introduced. As used herein the term "transfection" refers to the delivery of DNA into eukaryotic (e.g., mammalian) cells. The term "transformation" is used herein to refer to delivery of DNA into prokaryotic (e.g., E. coli) cells. The term "transduction" is used herein to refer to infecting cells with viral particles. The nucleic acid molecule can be stably integrated into the genome generally known in the art. Known methods of PCR include, but are not limited to, methods using paired primers, nested primers, single specific primers, degenerate primers, gene-specific primers, vector-specific primers, partially mismatched primers, and the like. For example, "transformed," "transformant," and "transgenic" cells have been through the transformation process and contain a foreign gene integrated into their chromosome. The term "untransformed" refers to normal cells that have not been through the transformation process.

"Genetically altered cells" denotes cells which have been modified by the introduction of recombinant or heterologous nucleic acids (e.g., one or more DNA constructs or their RNA counterparts) and further includes the progeny of such cells which retain part or all of such genetic modification.

As used herein, the term "derived" or "directed to" with respect to a nucleotide molecule means that the molecule has complementary sequence identity to a particular molecule of interest.

The siRNAs of the present invention can be generated by any method known to the art, for example, by in vitro transcription, recombinantly, or by synthetic means. In one example, the siRNAs can be generated in vitro by using a recombinant enzyme, such as T7 RNA polymerase, and DNA oligonucleotide templates.

Nucleic Acid Molecules of the Invention

The terms "isolated and/or purified" refer to in vitro isolation of a nucleic acid, e.g., a DNA or RNA molecule from its natural cellular environment, and from association with other components of the cell, such as nucleic acid or polypeptide, so that it can be sequenced, replicated, and/or expressed. The RNA or DNA is "isolated" in that it is free from at least one contaminating nucleic acid with which it is normally associated in the natural source of the RNA or DNA and is preferably substantially free of any other mammalian RNA or DNA. The phrase "free from at least one contaminating source nucleic acid with which it is normally associated" includes the case where the nucleic acid is reintroduced into the source or natural cell but is in a different chromosomal location or is otherwise flanked by nucleic acid sequences not normally found in the source cell, e.g., in a vector or plasmid.

In addition to a DNA sequence encoding a siRNA, the nucleic acid molecules of the invention include double-stranded interfering RNA molecules, which are also useful to inhibit expression of a target gene.

As used herein, the term "recombinant nucleic acid", e.g., "recombinant DNA sequence or segment" refers to a nucleic acid, e.g., to DNA, that has been derived or isolated from any appropriate cellular source, that may be subsequently chemically altered in vitro, so that its sequence is not naturally occurring, or corresponds to naturally occurring sequences that are not positioned as they would be positioned in a genome which has not been transformed with exogenous DNA. An example of preselected DNA "derived" from a source would be a DNA sequence that is identified as a useful fragment within a given organism, and which is then chemically synthesized in essentially pure form. An example of such DNA "isolated" from a source would be a useful DNA sequence that is excised or removed from a source by chemical means, e.g., by the use of restriction endonucleases, so that it can be further manipulated, e.g., amplified, for use in the invention, by the methodology of genetic engineering. "Recombinant DNA" includes completely synthetic DNA sequences, semi-synthetic DNA sequences, DNA sequences isolated from biological sources, and DNA sequences derived from RNA, as well as mixtures thereof.

Expression Cassettes of the Invention

To prepare expression cassettes, the recombinant DNA sequence or segment may be circular or linear, double-stranded or single-stranded. Generally, the DNA sequence or segment is in the form of chimeric DNA, such as plasmid DNA or a vector that can also contain coding regions flanked by control sequences that promote the expression of the recombinant DNA present in the resultant transformed cell.

A "chimeric" vector or expression cassette, as used herein, means a vector or cassette including nucleic acid sequences from at least two different species, or has a nucleic acid sequence from the same species that is linked or associated in a manner that does not occur in the "native" or wild type of the species.

Aside from recombinant DNA sequences that serve as transcription units for an RNA transcript, or portions thereof, a portion of the recombinant DNA may be untranscribed, serving a regulatory or a structural function. For example, the recombinant DNA may have a promoter that is active in mammalian cells.

Other elements functional in the host cells, such as introns, enhancers, polyadenylation sequences and the like, may also be a part of the recombinant DNA. Such elements may or may not be necessary for the function of the DNA, but may provide improved expression of the DNA by affecting transcription, stability of the siRNA, or the like. Such elements may be included in the DNA as desired to obtain the optimal performance of the siRNA in the cell.

Control sequences are DNA sequences necessary for the expression of an operably linked coding sequence in a particular host organism. The control sequences that are suitable for prokaryotic cells, for example, include a promoter, and optionally an operator sequence, and a ribosome binding site. Eukaryotic cells are known to utilize promoters, polyadenylation signals, and enhancers.

Operably linked nucleic acids are nucleic acids placed in a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation. Generally, operably linked DNA sequences are DNA sequences that are linked are contiguous. However, enhancers do not have to be contiguous. Linking is accomplished by ligation at convenient restriction sites. If such sites do not exist, the synthetic oligonucleotide adaptors or linkers are used in accord with conventional practice.

The recombinant DNA to be introduced into the cells may contain either a selectable marker gene or a reporter gene or both to facilitate identification and selection of expressing cells from the population of cells sought to be transfected or infected through viral vectors. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neo and the like.

Reporter genes are used for identifying potentially transfected cells and for evaluating the functionality of regulatory sequences. Reporter genes that encode for easily assayable proteins are well known in the art. In general, a reporter gene is a gene that is not present in or expressed by the recipient organism or tissue and that encodes a protein whose expression is manifested by some easily detectable property, e.g., enzymatic activity. For example, reporter genes include the chloramphenicol acetyl transferase gene (cat) from Tn9 of E. coli and the luciferase gene from firefly Photinus pyralis. Expression of the reporter gene is assayed at a suitable time after the DNA has been introduced into the recipient cells.

The general methods for constructing recombinant DNA that can transfect target cells are well known to those skilled in the art, and the same compositions and methods of construction may be utilized to produce the DNA useful herein.

The recombinant DNA can be readily introduced into the host cells, e.g., mammalian, bacterial, yeast or insect cells by transfection with an expression vector composed of DNA encoding the siRNA by any procedure useful for the introduction into a particular cell, e.g., physical or biological methods, to yield a cell having the recombinant DNA stably integrated into its genome or existing as a episomal element, so that the DNA molecules, or sequences of the present invention are expressed by the host cell. Preferably, the DNA is introduced into host cells via a vector. The host cell is preferably of eukaryotic origin, e.g., plant, mammalian, insect, yeast or fungal sources, but host cells of non-eukaryotic origin may also be employed.

Physical methods to introduce a preselected DNA into a host cell include calcium phosphate precipitation, lipofection, particle bombardment, microinjection, electroporation, and the like. Biological methods to introduce the DNA of interest into a host cell include the use of DNA and RNA viral vectors. For mammalian gene therapy, as described herein below, it is desirable to use an efficient means of inserting a copy gene into the host genome. Viral vectors, and especially retroviral vectors, have become the most widely used method for inserting genes into mammalian, e.g., human cells. Other viral vectors can be derived from poxviruses, herpes simplex virus I, adenoviruses and adeno-associated viruses, and the like. See, for example, U.S. Pat. Nos. 5,350,674 and 5,585,362.

As discussed herein, a "transfected" "or "transduced" host cell or cell line is one in which the genome has been altered or augmented by the presence of at least one heterologous or recombinant nucleic acid sequence. The host cells of the present invention are typically produced by transfection with a DNA sequence in a plasmid expression vector, a viral expression vector, or as an isolated linear DNA sequence. The transfected DNA can become a chromosomally integrated recombinant DNA sequence, which is composed of sequence encoding the siRNA.

To confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

To detect and quantitate RNA produced from introduced recombinant DNA segments, RT-PCR may be employed. In this application of PCR, it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique demonstrates the presence of an RNA species and gives information about the integrity of that RNA. The presence or absence of an RNA species can also be determined using dot or slot blot Northern hybridizations. These techniques are modifications of Northern blotting and only demonstrate the presence or absence of an RNA species.

While Southern blotting and PCR may be used to detect the recombinant DNA segment in question, they do not provide information as to whether the preselected DNA segment is being expressed. Expression may be evaluated by specifically identifying the peptide products of the introduced recombinant DNA sequences or evaluating the phenotypic changes brought about by the expression of the introduced recombinant DNA segment in the host cell.

The instant invention provides a cell expression system for expressing exogenous nucleic acid material in a mammalian recipient. The expression system, also referred to as a "genetically modified cell," comprises a cell and an expression vector for expressing the exogenous nucleic acid material. The genetically modified cells are suitable for administration to a mammalian recipient, where they replace the endogenous cells of the recipient. Thus, the preferred genetically modified cells are non-immortalized and are non-tumorigenic.

According to one embodiment, the cells are transfected or otherwise genetically modified ex vivo. The cells are isolated from a mammal (preferably a human), nucleic acid introduced (i.e., transduced or transfected in vitro) with a vector for expressing a heterologous (e.g., recombinant) gene encoding the therapeutic agent, and then administered to a mammalian recipient for delivery of the therapeutic agent in situ. The mammalian recipient may be a human and the cells to be modified are autologous cells, i.e., the cells are isolated from the mammalian recipient.

According to another embodiment, the cells are transfected or transduced or otherwise genetically modified in vivo. The cells from the mammalian recipient are transduced or transfected in vivo with a vector containing exogenous nucleic acid material for expressing a heterologous (e.g., recombinant) gene encoding a therapeutic agent and the therapeutic agent is delivered in situ.

As used herein, "exogenous nucleic acid material" refers to a nucleic acid or an oligonucleotide, either natural or synthetic, which is not naturally found in the cells; or if it is naturally found in the cells, is modified from its original or native form. Thus, "exogenous nucleic acid material"

includes, for example, a non-naturally occurring nucleic acid that can be transcribed into an anti-sense RNA, a siRNA, as well as a "heterologous gene" (i.e., a gene encoding a protein that is not expressed or is expressed at biologically insignificant levels in a naturally-occurring cell of the same type). To illustrate, a synthetic or natural gene encoding human erythropoietin (EPO) would be considered "exogenous nucleic acid material" with respect to human peritoneal mesothelial cells since the latter cells do not naturally express EPO. Still another example of "exogenous nucleic acid material" is the introduction of only part of a gene to create a recombinant gene, such as combining an regulatable promoter with an endogenous coding sequence via homologous recombination.

The condition amenable to gene inhibition therapy may be a prophylactic process, i.e., a process for preventing disease or an undesired medical condition. Thus, the instant invention embraces a system for delivering siRNA that has a prophylactic function (i.e., a prophylactic agent) to the mammalian recipient.

Methods for Introducing the Expression Cassettes of the Invention into Cells

The inhibitory nucleic acid material (e.g., an expression cassette encoding siRNA directed to a gene of interest) can be introduced into the cell ex vivo or in vivo by genetic transfer methods, such as transfection or transduction, to provide a genetically modified cell. Various expression vectors (i.e., vehicles for facilitating delivery of exogenous nucleic acid into a target cell) are known to one of ordinary skill in the art.

As used herein, "transfection of cells" refers to the acquisition by a cell of new nucleic acid material by incorporation of added DNA. Thus, transfection refers to the insertion of nucleic acid into a cell using physical or chemical methods. Several transfection techniques are known to those of ordinary skill in the art including calcium phosphate DNA co-precipitation, DEAE-dextran, electroporation, cationic liposome-mediated transfection, tungsten particle-facilitated microparticle bombardment, and strontium phosphate DNA co-precipitation.

In contrast, "transduction of cells" refers to the process of transferring nucleic acid into a cell using a DNA or RNA virus. A RNA virus (i.e., a retrovirus) for transferring a nucleic acid into a cell is referred to herein as a transducing chimeric retrovirus. Exogenous nucleic acid material contained within the retrovirus is incorporated into the genome of the transduced cell. A cell that has been transduced with a chimeric DNA virus (e.g., an adenovirus carrying a cDNA encoding a therapeutic agent), will not have the exogenous nucleic acid material incorporated into its genome but will be capable of expressing the exogenous nucleic acid material that is retained extrachromosomally within the cell.

The exogenous nucleic acid material can include the nucleic acid encoding the siRNA together with a promoter to control transcription. The promoter characteristically has a specific nucleotide sequence necessary to initiate transcription. The exogenous nucleic acid material may further include additional sequences (i.e., enhancers) required to obtain the desired gene transcription activity. For the purpose of this discussion an "enhancer" is simply any non-translated DNA sequence that works with the coding sequence (in cis) to change the basal transcription level dictated by the promoter. The exogenous nucleic acid material may be introduced into the cell genome immediately downstream from the promoter so that the promoter and coding sequence are operatively linked so as to permit transcription of the coding sequence. An expression vector can include an exogenous promoter element to control transcription of the inserted exogenous gene. Such exogenous promoters include both constitutive and regulatable promoters.

Naturally-occurring constitutive promoters control the expression of essential cell functions. As a result, a nucleic acid sequence under the control of a constitutive promoter is expressed under all conditions of cell growth. Constitutive promoters include the promoters for the following genes which encode certain constitutive or "housekeeping" functions: hypoxanthine phosphoribosyl transferase (HPRT), dihydrofolate reductase (DHFR), adenosine deaminase, phosphoglycerol kinase (PGK), pyruvate kinase, phosphoglycerol mutase, the beta-actin promoter, and other constitutive promoters known to those of skill in the art. In addition, many viral promoters function constitutively in eukaryotic cells. These include: the early and late promoters of SV40; the long terminal repeats (LTRs) of Moloney Leukemia Virus and other retroviruses; and the thymidine kinase promoter of Herpes Simplex Virus, among many others.

Nucleic acid sequences that are under the control of regulatable promoters are expressed only or to a greater or lesser degree in the presence of an inducing or repressing agent, (e.g., transcription under control of the metallothionein promoter is greatly increased in presence of certain metal ions). Regulatable promoters include responsive elements (REs) that stimulate transcription when their inducing factors are bound. For example, there are REs for serum factors, steroid hormones, retinoic acid, cyclic AMP, and tetracycline and doxycycline. Promoters containing a particular RE can be chosen in order to obtain an regulatable response and in some cases, the RE itself may be attached to a different promoter, thereby conferring regulatability to the encoded nucleic acid sequence. Thus, by selecting the appropriate promoter (constitutive versus regulatable; strong versus weak), it is possible to control both the existence and level of expression of a nucleic acid sequence in the genetically modified cell. If the nucleic acid sequence is under the control of an regulatable promoter, delivery of the therapeutic agent in situ is triggered by exposing the genetically modified cell in situ to conditions for permitting transcription of the nucleic acid sequence, e.g., by intraperitoneal injection of specific inducers of the regulatable promoters which control transcription of the agent. For example, in situ expression of a nucleic acid sequence under the control of the metallothionein promoter in genetically modified cells is enhanced by contacting the genetically modified cells with a solution containing the appropriate (i.e., inducing) metal ions in situ.

Accordingly, the amount of siRNA generated in situ is regulated by controlling such factors as the nature of the promoter used to direct transcription of the nucleic acid sequence, (i.e., whether the promoter is constitutive or regulatable, strong or weak) and the number of copies of the exogenous nucleic acid sequence encoding a siRNA sequence that are in the cell.

In addition to at least one promoter and at least one heterologous nucleic acid sequence encoding the siRNA, the expression vector may include a selection gene, for example, a neomycin resistance gene, for facilitating selection of cells that have been transfected or transduced with the expression vector.

Cells can also be transfected with two or more expression vectors, at least one vector containing the nucleic acid sequence(s) encoding the siRNA(s), the other vector containing a selection gene. The selection of a suitable promoter, enhancer, selection gene, and/or signal sequence is deemed to be within the scope of one of ordinary skill in the art without undue experimentation.

The following discussion is directed to various utilities of the instant invention. For example, the instant invention has utility as an expression system suitable for silencing the expression of gene(s) of interest.

The instant invention also provides methods for genetically modifying cells of a mammalian recipient in vivo. According to one embodiment, the method comprises introducing an expression vector for expressing a siRNA sequence in cells of the mammalian recipient in situ by, for example, injecting the vector into the recipient.

Delivery Vehicles for the Expression Cassettes of the Invention

The selection and optimization of a particular expression vector for expressing a specific miRNA in a cell can be accomplished by obtaining the nucleic acid sequence of the miRNA, possibly with one or more appropriate control regions (e.g., promoter, insertion sequence); preparing a vector construct comprising the vector into which is inserted the nucleic acid sequence encoding the miRNA; transfecting or transducing cultured cells in vitro with the vector construct; and determining whether the miRNA is present in the cultured cells.

Vectors for cell gene therapy include viruses, such as replication-deficient viruses (described in detail below). Exemplary viral vectors are derived from Harvey Sarcoma virus, ROUS Sarcoma virus, (MPSV), Moloney murine leukemia virus and DNA viruses (e.g., adenovirus).

Replication-deficient retroviruses are capable of directing synthesis of all virion proteins, but are incapable of making infectious particles. Accordingly, these genetically altered retroviral expression vectors have general utility for high-efficiency transduction of nucleic acid sequences in cultured cells, and specific utility for use in the method of the present invention. Such retroviruses further have utility for the efficient transduction of nucleic acid sequences into cells in vivo. Retroviruses have been used extensively for transferring nucleic acid material into cells. Protocols for producing replication-deficient retroviruses (including the steps of incorporation of exogenous nucleic acid material into a plasmid, transfection of a packaging cell line with plasmid, production of recombinant retroviruses by the packaging cell line, collection of viral particles from tissue culture media, and infection of the target cells with the viral particles) are well known in the art.

An advantage of using retroviruses for gene therapy is that the viruses insert the nucleic acid sequence encoding the siRNA into the host cell genome, thereby permitting the nucleic acid sequence encoding the siRNA to be passed on to the progeny of the cell when it divides. Promoter sequences in the LTR region have can enhance expression of an inserted coding sequence in a variety of cell types. Some disadvantages of using a retrovirus expression vector are (1) insertional mutagenesis, i.e., the insertion of the nucleic acid sequence encoding the miRNA into an undesirable position in the target cell genome which, for example, leads to unregulated cell growth and (2) the need for target cell proliferation in order for the nucleic acid sequence encoding the miRNA carried by the vector to be integrated into the target genome.

Another viral candidate useful as an expression vector for transformation of cells is the adenovirus, a double-stranded DNA virus. The adenovirus is infective in a wide range of cell types, including, for example, muscle and endothelial cells.

Adenoviruses (Ad) are double-stranded linear DNA viruses with a 36 kb genome. Several features of adenovirus have made them useful as transgene delivery vehicles for therapeutic applications, such as facilitating in vivo gene delivery. Recombinant adenovirus vectors have been shown to be capable of efficient in situ gene transfer to parenchymal cells of various organs, including the lung, brain, pancreas, gallbladder, and liver. This has allowed the use of these vectors in methods for treating inherited genetic diseases, such as cystic fibrosis, where vectors may be delivered to a target organ. In addition, the ability of the adenovirus vector to accomplish in situ tumor transduction has allowed the development of a variety of anticancer gene therapy methods for non-disseminated disease. In these methods, vector containment favors tumor cell-specific transduction.

Like the retrovirus, the adenovirus genome is adaptable for use as an expression vector for gene therapy, i.e., by removing the genetic information that controls production of the virus itself. Because the adenovirus functions in an extrachromosomal fashion, the recombinant adenovirus does not have the theoretical problem of insertional mutagenesis.

Several approaches traditionally have been used to generate the recombinant adenoviruses. One approach involves direct ligation of restriction endonuclease fragments containing a nucleic acid sequence of interest to portions of the adenoviral genome. Alternatively, the nucleic acid sequence of interest may be inserted into a defective adenovirus by homologous recombination results. The desired recombinants are identified by screening individual plaques generated in a lawn of complementation cells.

Thus, as will be apparent to one of ordinary skill in the art, a variety of suitable viral expression vectors are available for transferring exogenous nucleic acid material into cells. The selection of an appropriate expression vector to express a therapeutic agent for a particular condition amenable to gene silencing therapy and the optimization of the conditions for insertion of the selected expression vector into the cell, are within the scope of one of ordinary skill in the art without the need for undue experimentation.

In another embodiment, the expression vector is in the form of a plasmid, which is transferred into the target cells by one of a variety of methods: physical (e.g., microinjection, electroporation, scrape loading, microparticle bombardment) or by cellular uptake as a chemical complex (e.g., calcium or strontium co-precipitation, complexation with lipid, complexation with ligand). Several commercial products are available for cationic liposome complexation including Lipofectin™ (Gibco-BRL, Gaithersburg, Md.) and Transfectam™ (Promega®, Madison, Wis.). However, the efficiency of transfection by these methods is highly dependent on the nature of the target cell and accordingly, the conditions for optimal transfection of nucleic acids into cells using the herein-mentioned procedures must be optimized. Such optimization is within the scope of one of ordinary skill in the art without the need for undue experimentation.

Administration of Cells to Subject

The modified cells of the present invention can be formulated as pharmaceutical compositions. Cells are derived from somatic tissue and used in a two or three step process to induce gene expression and cell differentiation or cell type conversion. Reprogrammed cells or converted cells have a gene and/or microRNA expressed that does not harm the individual and is biological. These reprogrammed cells can be used for tissue regeneration, tissue repair, bone regeneration, palate regeneration, cartilage regeneration and repair. Also used to inhibit inflammation and bone resorption. Alternatively, human tissue can be directly modified by addition of the reagents (transcription factors and microRNAs per the combinations and processes outlined in this application) and administered to a mammalian host, such as in the form of a graft, in a scaffold, as single cells or implants. In certain embodiments, the cells are administered to a human patient in a form adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of the invention formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Compounds of the invention can also be administered in combination with other therapeutic agents, for example, other agents that are useful for the reprogramming of different types of cells and tissues. Examples of such agents include specific microRNAs and transcription factors or signaling factors. Accordingly, in one embodiment the invention also provides a composition comprising a compound of formula I, or a pharmaceutically acceptable salt thereof, at least one other therapeutic agent, and a pharmaceutically acceptable diluent or carrier. The invention also provides a kit comprising a compound of formula I, or a pharmaceutically acceptable salt thereof, at least one other therapeutic agent, packaging material, and instructions for administering the compound of formula I or the pharmaceutically acceptable salt thereof and the other therapeutic agent or agents to an animal to cure cancer, alleviate pain and inflammation, regenerate tissues and bone and cartilage.

The invention will now be illustrated by the following non-limiting Example.

Example 1

A Pituitary Homeobox 2 (Pia2):microRNA-200a-3p:Beta-Catenin Pathway Converts Mesenchyme Cells to Amelogenin-Expressing Dental Epithelial Cells Background: An efficient method is required for converting somatic cells to specific cell fates.
Results: A combination of Pitx2 and miR-200a-3p promotes dental epithelial gene expression in cells.
Conclusion: A two-step method efficiently converts mesenchyme cells to dental epithelial cells.
Significance: A new method to generate dental epithelial cells, which are difficult to isolate, is identified for use in regeneration and repair.

Pitx2, Wnt/β-catenin signaling and microRNAs (miRs) play a critical role in the regulation of dental stem cells during embryonic development. As described herein, a Pitx2:β-catenin regulatory pathway involved in epithelial cell differentiation and conversion of mesenchyme cells to amelogenin expressing epithelial cells via miR-200a has been identified. Pitx2 and β-catenin are expressed in the labial incisor cervical loop (LaCL) or epithelial stem cell niche, with decreased expression in the differentiating ameloblast cells of the mouse lower incisor. Bioinformatics analyses reveal that miR-200a-3p expression is activated in the pre-ameloblast cells to enhance epithelial cell differentiation. We demonstrate that Pitx2 activates miR-200a-3p expression and miR-200a-3p reciprocally represses Pitx2 and β-catenin expression. Pitx2 and β-catenin interact to synergistically activate gene expression during odontogenesis and miR-200a-3p attenuates their expression and directs differentiation. To understand how this mechanism controls cell differentiation and cell fate, oral epithelial and odontoblast mesenchyme cells were reprogrammed by a two-step induction method using Pitx2 and miR-200a-3p. Conversion to dental amelogenin expressing epithelial cells involved an up-regulation of the stem cell marker Sox2 and proliferation genes and decreased expression of mesenchymal markers. E-cadherin expression was increased as well as ameloblast specific factors. The combination of Pitx2, a regulator of dental stem cells and miR-200a converts mesenchyme cells to a fully differentiated dental epithelial cell type. This pathway and reprogramming can be used to reprogram mesenchyme or oral epithelial cells to dental epithelial (ameloblast) cells, which can be used in tissue repair and regeneration studies.

Introduction

The epithelial stem cells that control growth of the rodent incisor are located in the cervical loop (a stem cell niche) at the posterior end of the incisor (1). The cervical loop consists of the inner enamel epithelium, outer enamel epithelium, and stellate reticulum cells in the core of the cervical loop and a thin layer of stratum intermedium cells (2,3). The stem cells in the core of the cervical loop will divide and insert into the basal layer of epithelium, the outer enamel epithelium. They will proliferate as transit amplifying cells and then differentiate to ameloblasts cells, which secrete enamel. The labial epithelial stem cells differentiate to ameloblasts while odontoblasts originate from mesenchymal stem cells and secrete dentin on both sides of incisor. A signaling network has been proposed to regulate epithelial stem cell proliferation in the cervical loop stem cell niche (4). These signals originate from mesenchymal tissue derived from the neural crest cells to regulate epithelial stem cells in concert with epithelial signals.

The signaling molecules include fibroblast growth factor (Fgf) 8, expressed in pre-tooth epithelium and bone morphogenic protein (Bmp) 4, expressed in intervening epithelium and their interaction and competing actions specify tooth formation (5,6). Fgf and Bmp regulate restricted expression of the homeobox transcription factor Pitx2 that is required for tooth development (7). Wnts comprise a large family of secreted ligands that activate several receptor-mediated pathways (8). The well-known canonical Wnt/β-catenin pathway activation causes β-catenin accumulation, nuclear translocation and transcriptional activation by complexes of β-catenin, Lef/Tcf and Pitx2 transcription factor family members (8-10). Activation of Wnt/β-catenin signaling initiates the de novo formation of hair follicles, feather buds, mammary placodes, taste buds and teeth (4,11-17). Wnt/β-catenin signaling is required for multiple stages of tooth development and dental epithelial cell proliferation and differentiation (14). The Lef-1 transcription factor regulates genes involved in cell proliferation and differentiation. Lef-1 deficiency causes arrested tooth development at the bud stage in mice and the dental epithelial cells fail to survive (18,19).

miRs are non-coding small RNAs that regulate gene function post-transcriptionally. Animal miRs are imperfectly paired to the 3'UTR of target mRNA and inhibit protein production either through destabilization of mRNA or inhibition of translation (20). Tooth development including epithelium stem cell differentiation is tightly controlled by miRs and a loss of mature miRs results in the development of supernumerary incisors in the Dicer conditional knockout mouse (21,22). miRs control stem cell differentiation in the incisor and miR depletion causes an expansion and increased proliferation of dental stem cells (21).

The miR 200 family regulates the epithelial-mesenchymal transition (EMT) associated with tumor cell migration, invasion, adhesion and metastasis (23). The miR 200 family targets and represses the expression of genes involved in this process. These genes include Zeb1, Zeb2, and Jagged1 (23-29). The miR 200 family is selectively expressed in differentiating dental epithelial cells and have low levels of expression in the dental stem cell niche (21,22,30). The miR 200 family comprise five members, miR-429-200a-200b in one cluster and miR-200c-141 in another cluster located on different chromosomes. We recently reported a Pitx2:miR-200c/141:Noggin pathway regulated Bmp signaling and epithelial cell differentiation during odontogenesis (31). Thus, Pitx2 and miR 200 appear to control the fate of dental stem cells.

There are many protocols used for regeneration therapies to develop fully functioning organs including teeth. Current tooth bioengineering relies on the sequential and reciprocal interactions between neural crest-derived mesenchyme cells and stomadial epithelium, in vitro differentiation of dental epithelial progenitor cells through epithelial-mesenchyme interactions and tooth organ germ bioengineering from molar tooth germ-derived epithelial and mesenchyme cells (3,32-37). However, for replacement of a functional tooth these tissues are difficult to obtain and maintain in culture. Mesenchymal stem cells derived from bone marrow and dental pulp stem cells are used to make dental cells and tissues, repair dental structures and regenerate bone (38-42). Stem cells have great promise in tissue bioengineering studies, but they are difficult to obtain. Additional, more efficient methods are needed for generating dental cells.

The discovery that fibroblast cells can be converted to induced-pluripotent cells by induction of a cocktail of transcription factors has led to the development of cell reprogramming for tissue engineering (43). miRs have also evolved as regulators of gene programs that control cell differentiation and cell fate decisions (44). miRs modulate these functions through positive and negative feedback loops to reinforce cellular decisions (45).

Because dental stem cells are difficult to obtain, culture and propagate as well as producing human epithelial-mesenchyme tooth forming tissues, a new method of using a combination of transcription factor and miRs in a sequential addition to both oral epithelial cells and odonotblast mesenchyme cells to produce amelogenin producing dental epithelial cells is proposed, as described herein.

Experimental Procedures

Expression and Reporter Constructs

The expression plasmids containing the cytomegalovirus (CMV) promoter linked to the mmu-miR-200a and mmu-miR-21 precursor were constructed in pSilencer 4.1 (Ambion). Pitx2, and β-catenin S37A expression plasmids were constructed in pcDNA 3.1 MycHisC (Invitrogen) as described previously (46-49). Pitx2 3'-UTR and Pitx2 mutant 3'-UTR generated by mutagenesis (QuickChange Site-Directed mutagenesis kit, Agilent Technologies) were directionally cloned into the pGL3 CXCR4 1P (Addgene, plasmid 11310). The 7×TopFlash reporter plasmid was constructed into luciferase vector by inserting seven Lef/Tcf binding sites upstream of the minimal thymidine kinase promoter. The FopFlash reporter, which has the Lef/Tcf binding sites mutated, was also constructed in the luciferase vector (50). The Pitx2c 3kb and Lef-1 promoters have been reported previously (9,51). All constructs were confirmed by DNA sequencing.

Cell Culture, Transient Transfections, Luciferase, and β-Galactosidase Assays

HEK 293 FT, MDPC and LS-8 cells were cultured in DMEM supplemented with 5 or 10% FBS and penicillin/streptomycin and transfected by electroporation or lipofectin. The procedures for transient transfections and luciferase and β-galactosidase assays were described previously (46). Transfected cells were incubated for 48 h. LiCl was added to the appropriate cells at a final concentration of 10 mM 23 h before harvest. The pcDNA3.1 empty vector, pLL3.7 or pSilencer 4.1 negative control vectors were added to equalize the total amount of cotransfected expression vectors. SV-40 or CMV β-galactosidase reporter plasmids were co-transfected in all experiments as a control for transfection efficiency. All plasmids were double-banded CsCl purified.

Generation of MDPC and LS-8 miR-200a Stable Cell Lines

Fragments containing the miR-200a precursor were amplified by PCR and directionally cloned into the EcoRI site of pLL3.7. Lentivirus was generated by cotransfection of the above construct with packaging plasmids into HEK293T cells, as described previously (31). Blastomycin (5 µg/ml) was added to cells for 5 days and surviving cells were propagated and subcultured. MDPC and LS-8 cells were transduced and subsequently FACS-sorted for green fluorescent protein (GFP), which is co-expressed on a single transcript with the miR.

Chromatin Immunoprecipitation (ChIP) Analysis

The ChIP analysis was performed as described (52) using the ChIP assay kit (Upstate Biotechnology, Inc.) with the following modifications. LS-8 cells were fed for 24 h, harvested, and plated in 60-mm dishes. Cells were cross-linked with 1% formaldehyde for 10 min at 37° C. the next day. Samples were incubated with PITX2ABC rabbit polyclonal antibody (CAPRA SCIENCE) overnight at 4° C. Immune complexes were washed consecutively for 5 min with each of the following solutions: low salt immune complex wash buffer, high salt immune complex wash buffer four times, and LiCl immune complex wash buffer and TE buffer twice. An aliquot of the immunoprecipitated DNA from non-transfected cells was used for PCR (32 cycles). All reactions were done at an annealing temperature of 61° C. Two primers for amplifying the Pitx2 binding site in the miR-200a promoter are as follows: sense, 5'TTCTTGGCTCTGTATGGGAGA-3' (SEQ ID NO: 6); antisense, 5'-CCCCTCTTGCCTTTTTCAG-3' (SEQ ID NO: 7). All of the PCR products were evaluated on a 1% agarose gel in 1×TBE for appropriate size (175 bp) and confirmed by sequencing. As controls, the primers were used without chromatin, and normal rabbit IgG was used replacing the PITX2 antibody to reveal nonspecific immunoprecipitation of the chromatin. Furthermore, the same set of experiments was done with control primers targeting the distal region of miR-200a promoter lacking putative Pitx2 binding sites. The control primers are as follows: sense, 5'AGGCAACAGACACCTGCACT-3' (SEQ ID NO: 8); antisense, 5'-GAATGACTGTCTCCCCTCCA-3' (SEQ ID NO: 9).

Mouse Tissue Isolation and Real-Time PCR Analyses

The PITX2C cDNA was cloned into the K14 promoter construct (53). We placed the hrGFP (humanized Renilla GFP) gene in the cassette to observe expression in live cells and have observed good expression of PITX2C in transgenic mice by PCR. The PITX2C GFP DNA was excised from the plasmid and used for pronuclear injection. Donor female mice (FVB/NCr), stud male (FVB/NCr), vasectomized male (ICR) and recipient female (ICR) were used in the experiments. Multiple founders were analyzed for transgene expression and crossed to BL6 mice and re-evaluated for expression (54). All animals were housed in the Program of Animal Resources of the Institute of Biosciences and Technology, and were handled in accordance with the principles and procedure of the Guide for the Care and Use of Laboratory Animals. The Texas A&M Health Science Center, Institutional Animal Care and Use Committee approved all experimental procedures. Wild type (C57BL/6) and K14-PITX2C transgenic mouse mandible, maxilla and palate tissues were harvested at various developmental time points, and total RNA prepared for analyses of gene and miR expression. These tissues were harvested using modified procedures for isolating epithelial stem cells and tissue (21,31,55-58). After removing the skin from mouse heads, the hemi-mandibles and maxilla are isolated by removing muscle, tendons, ligaments and bones using a scalpel under a dissecting microscope. The incisors and molars are further dissected from bone. The incisors and molars are incubated in Dispase II and Collagenase I for 30 minutes at 37° C. to separate epithelium from mesenchyme. Total RNAs were prepared using the RNeasy minikit from Qiagen. The amount and integrity of the RNA samples were assessed by measurement at 260 and 280 nm and gel analyses. LS-8 (59) or MDPC (60) cells transfected with pLL-scramble or pLL-miR-200a precursor stable cell lines were harvested 48 h after seed. Total RNA was reverse transcribed into cDNA by the iScript Select cDNA Synthesis kit (Bio-Rad). Real-time PCR was carried out in a total reaction of 25 µl containing 12.5 µl of iQ SYBR Green Supermix, 0.1 µM forward primer, 0.1 µM reverse primer, 0.25 µl of cDNA template in the MyiQ Singlecolor real-time detection system and analyzed by the MyiQ optical system software 2.0 (Bio-Rad). β-Actin served as a reference gene for normalization of E-cadherin mRNA levels. Lef-1 primer sequences were 5'-GCAGCTATCAACCAGATCC-3 (SEQ ID NO: 10) (forward) and 5'-GATGTAGGCAGCTGTCATTC-3 (SEQ ID NO: 11) (reverse); E-cadherin primer sequences were 5'-GCTTCAGTTCCGAGGTCTAC-3' (SEQ ID NO: 12) (forward) and 5'-AGATGCCGCTTCACTTGTGAT (SEQ ID NO: 13) (reverse); Cyclin D2 primer sequences were 5'-GAGCTGCTGGCCAAGATCAC (SEQ ID NO: 14) (forward) and 5'-GACTTGGATCCGGCGTTATG (SEQ ID NO: 15) (reverse) (50). Dog E-cadherin primer sequence were 5'-AGTGACTCGCAATGATGTGG-3' (SEQ ID NO: 16) (forward) and 5'-GAACCGCTTCCTTCATAGTC-3' (SEQ ID NO: 17) (reverse) and dog GAPDH primers sequence 5'-CATCACTGCCACCCAGAAG-3' (SEQ ID NO: 18) (forward) and 5'-CAGTGAGCTTCCCGTTCAG-3' (SEQ ID NO: 19) (reverse) (27). The thermal cycling profile consisted of 95° C. for 4 min, followed by 40 cycles of denaturation at 95° C. for 30 s, annealing at 60° C. for 30 s, and elongation at 72° C. for 18 s. Samples were run in triplicate. No-template control was run in each experiment. Melting curve analyses were performed to confirm amplification specificity of the PCR products, and all PCR products were sequenced to confirm their identity.

Western Blot Assays

Expression of endogenous Pitx2 and β-catenin proteins were demonstrated using the PITX2ABC antibody (CAPPA SCIENCE) and β-catenin antibodies (Millipore). Approximately 10-40 µg of transfected cell lysates or tissues were analyzed in Western blots. Following SDS gel electrophoresis, the proteins were transferred to PVDF filters (Millipore), immunoblotted and detected using specific antibodies and ECL reagents from GE HealthCare.

Immunofluorescent Staining

The pLL-Scramble, pLL-Pitx2, pLL-miR-200a, and pLL-Pitx2-miR-200a cells were plated onto fibronectin-coated chamber slides (BD Biosciences) and stained at day 12 or day 3, respectively. For E-cadherin and Amelogenin staining, cells were washed with PBS, fixed in ice-cold acetone for 10 min at 4° C. and air-dried. Fixed cells were washed with PBS for 2-5 min, incubated in 10% normal goat serum-PBS 30 min at room temperature (RT), then incubated cells with rat anti-E-cadherin or anti-Amelogenin antibodies at 4° C. overnight. After overnight incubation, cells were rinsed by washing in PBS for 3-5 min and cells were incubated with Alexa Fluor 488 goat anti-rat IgG (H+L) (Molecular Probes, labeling & detection by Life Technologies) 30 min at 37° C. Cells were washed with PBS for 3-5 min and mounted with VECTASHIELD Mounting Medium with DAPI (Vector Laboratories, Inc. Burlingame, Calif., USA). Images were acquired using a Nikon ECLIPSE 80i microscope and NIS-Elements AR3.2 software.

RNA Sequencing

Total RNA was isolated from LS-8 and MDPC-23 cell lines after transduction with virus and Fluorescence Activated Cell Sorted (FACS), using the miRNeasy Mini Kit (Qiagen) following the manufacturer's instructions. RNA quality and concentration was determined using the Agilent 321 Bioanalyzer (Agilent Technologies). Using 1 µg RNA and the TruSeq Stranded Total RNA Library Prep kit (Illumina), reverse transcription with bar-coded primers, complementary DNA amplification, and 100×100 paired ended sequencing with Illumina HiSeq 2000 were performed. Each sample had one biological duplicate that was barcoded separately and sequenced in an independent lane. Quality control of the obtained reads and mapping to the mouse reference genome (GRCm38/mm10) were performed using the combination of the Galaxy (https://main.g2.bx.psu.edu/) web-based analysis suite (61-63) and in-house Perl scripts. Mapped reads were analyzed using Cufflink tool set (64) to identify significant changes in gene expression. The low expression transcripts (less than 10 reads in all samples) were filtered out, and P values were adjusted using a threshold for false discovery rate (FDR) ≤0.001. Differentially expressed transcripts were identified using threshold of fold change≥2 and FDR≤0.001. The differentially expressed genes were further used for hierarchical clustering performed using Cluster 3.0, and Java Treeview was used for visualization (65,66). Gene ontology category enrichment was assessed using GOrilla (http://cbl-gorilla.cs.technion.ac.il/). Q-RT-PCR analysis for the genes indicated was compared with the RNA sequencing results. Amplification of VPS29 and Actin was used to normalize the values.

Results

Bioinformatics analyses of isolated murine dental epithelium and mesenchyme at different developmental stages identified gene and miR signatures. These data were then integrated into gene ontology category enrichment maps and used to identify processes that are common and different for dental epithelial cells compared to other cells. These data identified several new molecular mechanisms that control dental epithelial cell proliferation and differentiation. Pitx2 is the first transcriptional marker for tooth development and the miR-200 family is required for dental epithelial cell differentiation (6,21,31,67,68). A functional analyses of a new Pitx2-beta-catenin-miR-200a regulatory pathway identified in the bioinformatics analyses was first performed and then this new mechanism was used to convert both oral epithelial and dental mesenchyme cells to a dental epithelial cell fate. Thus, a method to convert oral epithelium and dental mesenchyme cells to dental epithelial cells is described herein, which express many genes that are hallmarks of these cells, including the expression of the ameloblast (differentiated dental epithelium) specific marker, amelogenin.

Figures 1A, 1B:
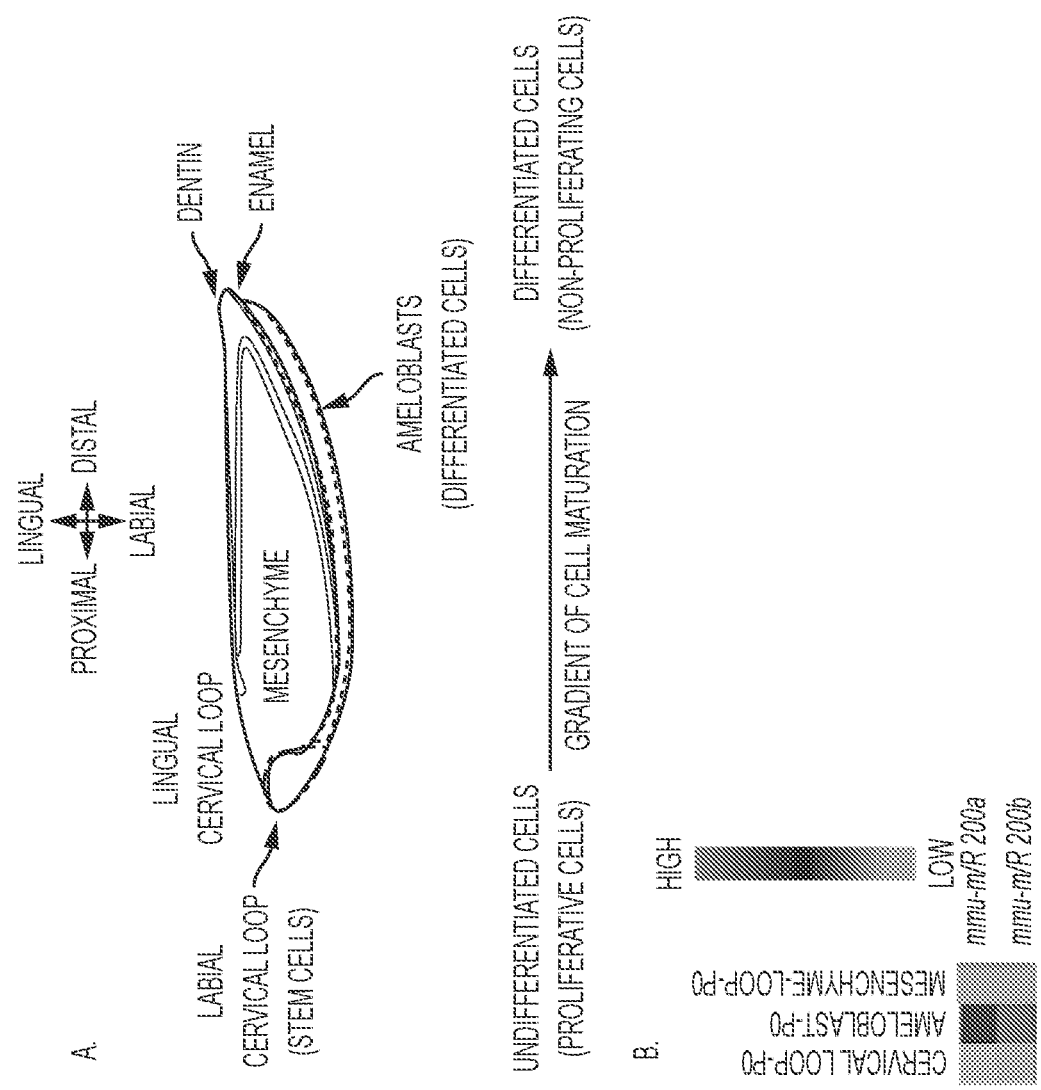
FIGS. 1A-1B. miR-200a-3p expression is associated with differentiating dental epithelial cells. A) Schematic of the mouse lower incisor cell and tissue structures. The black dotted line denotes the labial cervical loop (LaCL, stem cell niche), the red dotted line denotes the pre-secretory, secretory and mature differentiated epithelial tissues (pre-ameloblasts and ameloblasts). Green shaded region, mesenchyme; dark blue, dentin; orange, enamel. B) Heat map of selected miR-200a-3p and miR-200b-3p expression in the isolated dental epithelial tissue compartment (LaCL vs. Ameloblasts) and dental mesenchyme (Ameloblast vs. Mesenchyme). These tissues were isolated from P0 mice lower incisors, total RNA harvested and miRs analyzed by microRNA arrays. Five separate biological samples were analyzed.

Dental epithelial and mesenchyme tissue from P0 mouse incisors were isolated and screened for gene and miR expression to understand gene regulatory networks (GRN) and how dental stem cells yield fully differentiated epithelial cells or ameloblasts. The incisor labile cervical loop (LaCL) contains dental stem cells that give rise to the differentiated ameloblasts (FIG. 1A). The epithelial compartment was divided into the LaCl or undifferentiated cells (black dashed line) and the differentiating cells (red dashed line), while the dental mesenchyme was separated from the epithelium and total RNA was isolated for gene and miR expression analyses. A miR expression profile was identified showing that miR-200a and miR-200b were associated with differentiating epithelial cells (pre-ameloblast cells) (FIG. 1B). These miRs were not expressed in the dental mesenchyme suggesting that miR-200a and miR-200b may promote epithelial cell differentiation. However, their molecular mechanism in dental epithelial cell differentiation was not known. Analyses of miR-200a-3p binding elements identified Pitx2 and β-catenin as potential targets through sequences in their 3'UTRs (FIG. 2A). To demonstrate a functional miR-200a-3p regulation of Pitx2, the Pitx2 3'UTR was cloned into the luciferase vector and co-transfected in LS-8 oral epithelial cells with miR-200-3p or empty vector. miR-200a-3p repressed luciferase activity from the vector containing the Pitx2 3'UTR, but not when the miR-200a-3p target site was mutated in the Pitx2 3'UTR construct (FIG. 2B, C). Transfected miR-200a-3p decreased endogenous Pitx2 protein expression (Pitx2 isoforms) in LS-8 cells (FIG. 2D), and also decreased β-catenin protein expression in these cells (FIG. 2E)(69). Quantitation of multiple Western blots demonstrates significantly decreased Pitx2 and β-catenin protein expression in miR-200a transfected LS-8 oral epithelial cells (FIG. 2F). These data demonstrate that both Pitx2 and β-catenin are targeted by miR-200a-3p.

Figures 3A, 3B, 3C, 3D, 3E:
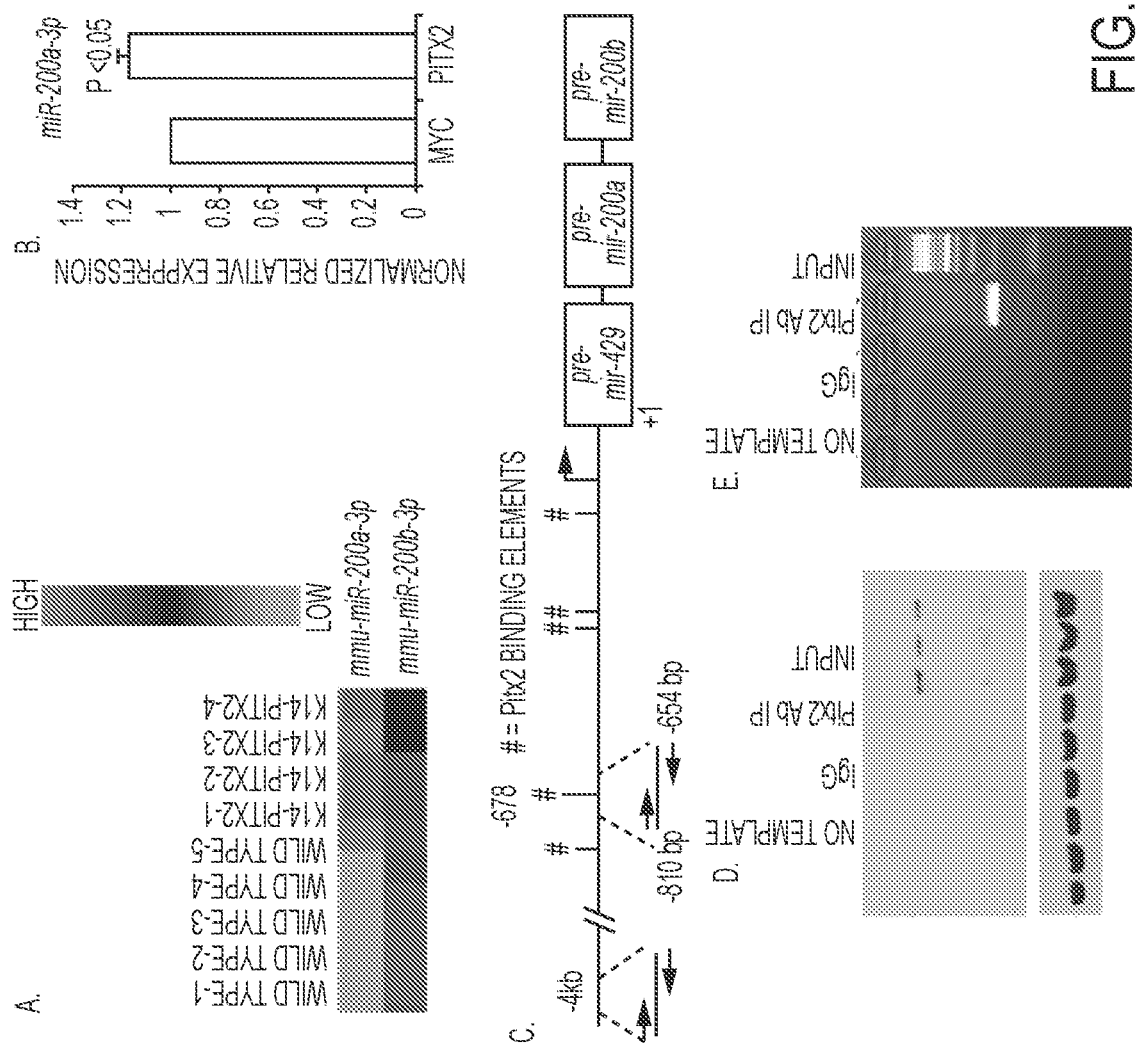
FIGS. 3A-3E. Endogenous Pitx2 binds to and activates the miR-200a promoter. A) Heat map of miR-200a-3p and miR-200b-3p expression in wild type and K-14-PITX2 over expression mouse lower incisor epithelial tissue. B) Real time PCR of endogenous miR-200a-3p expression in LS-8 cells transfected with empty vector (MYC) or PITX2. N=3. C) Schematic representation and location of the Pitx2 binding site in the mmu-miR-429-200a-200b promoter. # indicates the Pitx2 binding elements (TAATCC). D) ChIP of endogenous Pitx2 binding to the Pitx2 element approximately 678 bp upstream of pre-miR-429-200a-200b transcript in LS-8 cells. Rabbit antisera used as a control IP and Pitx2ABC antisera from CAPPA SCIENCE was used to IP Pitx2 binding to the chromatin. The input chromatin is shown as a positive control for the ChIP. E) Control ChIP using the Pitx2 antisera and primers to a 4 kb upstream region of the pre-miR-429-200a-200b transcript. This chromatin does not contain a Pitx2 binding site and was not IP'ed using Pitx2 antisera, the primers did amplify the input chromatin.

Mouse incisor P1 epithelial tissue from wild type (WT) and K14-PITX2C over expression mice was analyzed for miR expression by miR arrays. PITX2C over expression increased miR-200a and miR-200b expression in the dental epithelium (FIG. 3A). Sequence analyses of the 5' flanking region of the miR-429-200a-200b cluster identified a Pitx2 binding element (5'TAATCC-3'). Whether Pitx2 regulated miR-200a-3p expression was also investigated. Transfection of Pitx2C in LS-8 cells activated endogenous miR-200a-3p expression (FIG. 3B). Endogenous Pitx2 binding to the miR-200a promoter was characterized by chromatin immunoprecipitation assays (ChIP) in LS-8 cells. Pitx2 bound to a Pitx2 element in the 5' flanking region of the miR-200a chromatin (FIG. 3C) but not to an adjacent sequence. This sequence does not contain a Pitx2 binding site (FIGS. 3D and E, respectively). Thus, Pitx2 activates miR-200a-3p expression and miR-200a-3p acts to repress Pitx2 expression. This tight regulation of Pitx2 and miR-200a expression may be one mechanism to control dental epithelial differentiation.

Figures 4A, 4B, 4C, 4D:
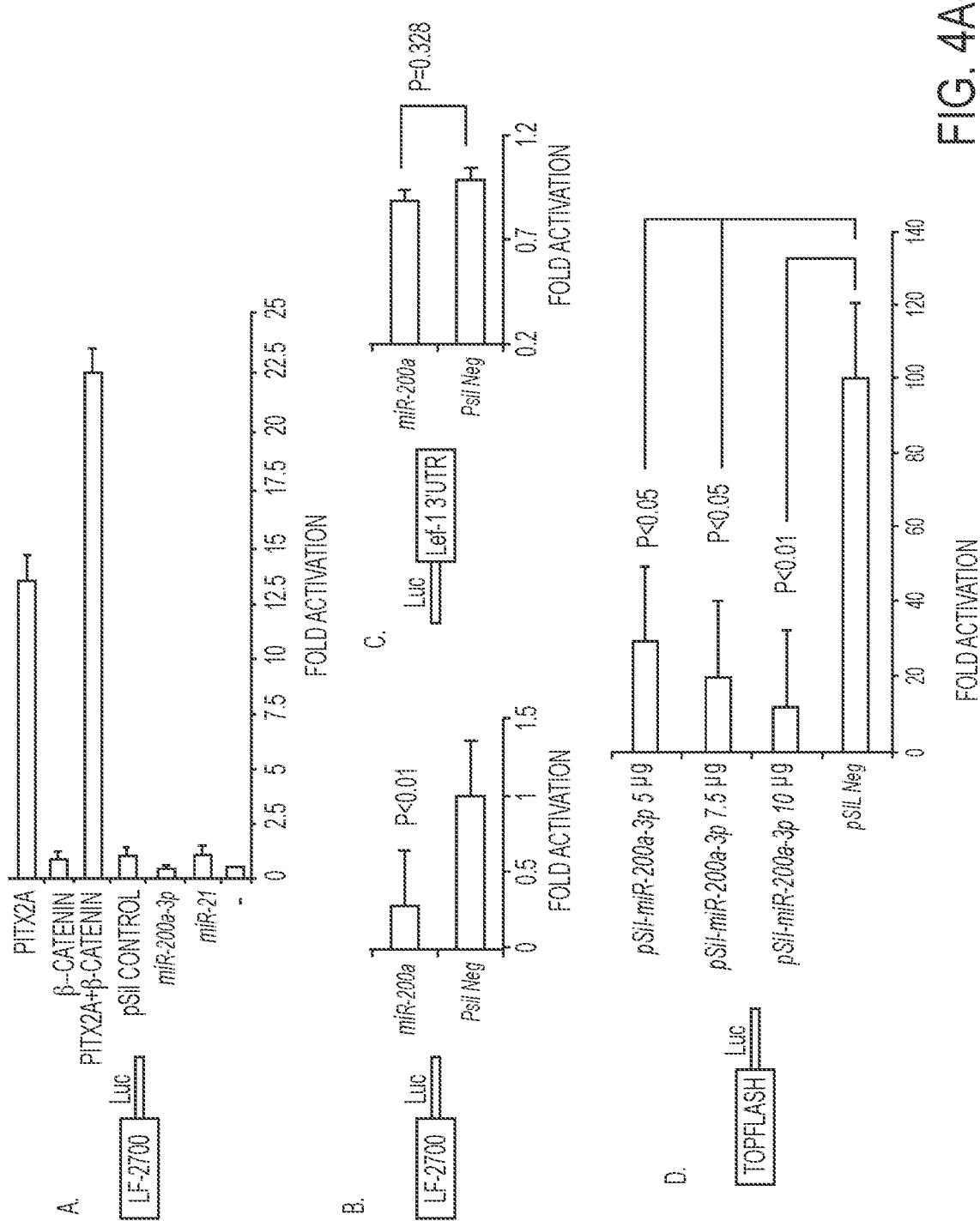
FIGS. 4A-4D. miR-200a-3p indirectly regulates the LEF-1 promoter and TopFlash reporter. A) miR-200a targets endogenous Pitx2 and β-catenin, which activate the LEF-1 promoter in LS-8 cells. The LEF-1 2.7 kb mouse promoter and Pitx2, β-catenin, pre-miR-200a, pSil-empty vector and pre-miR-21 were transfected in LS-8 cells. To control for transfection efficiency, all transfections included the SV-40 β-galactosidase reporter (0.5 µg). Cells were incubated for 48 h and then assayed for luciferase and β-galactosidase activities as previously described (10). The activities are shown as mean-fold activation compared with the luciferase plasmid with empty vector and normalized to β-galactosidase activity±S.E. from three independent experiments. B) miR-200a targets endogenous Pitx2 and represses Lef-1 activity in LS-8 cells. The LEF-1 promoter was transfected with miR-200a or pSil vector only in LS-8 cells, which endogenously express Pitx2 and β-catenin. Luciferase activity was assayed and miR-200a transfection was compared to vector only as in panel A. C) As a control the Lef-1 3'UTR luciferase construct was transfected with miR-200a or empty vector to demonstrate that miR-200a does not directly regulate Lef-1 expression. D) The TopFlash reporter (contains 7 Lef-1 binding elements, (50)) was co-transfected with increasing amounts of miR-200a-3p plasmid in LS-8 cells. Luciferase activity was measure as in panel A.

Wnt/β-catenin expression is required for tooth development at many stages and regulates incisor epithelial cell proliferation and differentiation (14). Pitx2 activates Lef-1 expression and in concert with β-catenin synergistically activates the LEF-1 promoter (FIG. 4A) (9). When LS-8 cells (which, endogenously express Pitx2 and β-catenin) were cotransfected with the LEF-1 promoter and miR-200a, luciferase activity from the LEF-1 promoter decreased compared to miR empty vector and miR-21 (used as controls) (FIG. 4A). A direct comparison of LEF-1 promoter activity with miR-200a expression revealed a 4-fold decrease in luciferase activity compared to empty vector (FIG. 4B). As a control we show that miR-200a does not regulate the Lef-1 3'UTR luciferase construct (FIG. 4C). Thus, miR-200a-3p indirectly regulates Lef-1 expression by inhibiting endogenous Pitx2 and β-catenin, which both activate endogenous Lef-1 expression. Titration of miR-200a-3p in LS-8 cells transfected with the TopFlash reporter decreased its luciferase activity compared to empty vector alone (FIG. 4D). The FopFlash reporter (LEF-1 binding sites mutated) was not affected by miR-200a-3p expression (data not shown). Thus, Pitx2 and β-catenin interact (9,10) to regulate Lef-1 expression and miR-200a-3p represses Pitx2 and β-catenin expression and indirectly represses Lef-1 expression and Wnt/β-catenin signaling mechanisms.

Pitx2 is highly expressed in the LaCL and regulates progenitor cell proliferation and differentiation during incisor development along with Lef-1 (7,14,18,31). Because miR-200a caused an MET response when over expressed in cells (27), it was investigated whether miR-200a-3p could cause the LS-8 oral epithelial-like cells to convert to dental epithelial cells that express E-cadherin. Furthermore, E-cadherin, which promotes epithelial cell differentiation also decreases β-catenin transcriptional activity (70). However, this E-cadherin repression of β-catenin can be counteracted by Pitx2 activation of Lef-1 expression. Thus, miR-200a induces E-cadherin expression and MET while Pitx2 acts to increase Lef-1 expression and cell proliferation.

Figures 5A, 5B, 5C, 5D, 5E, 5F, 5G:
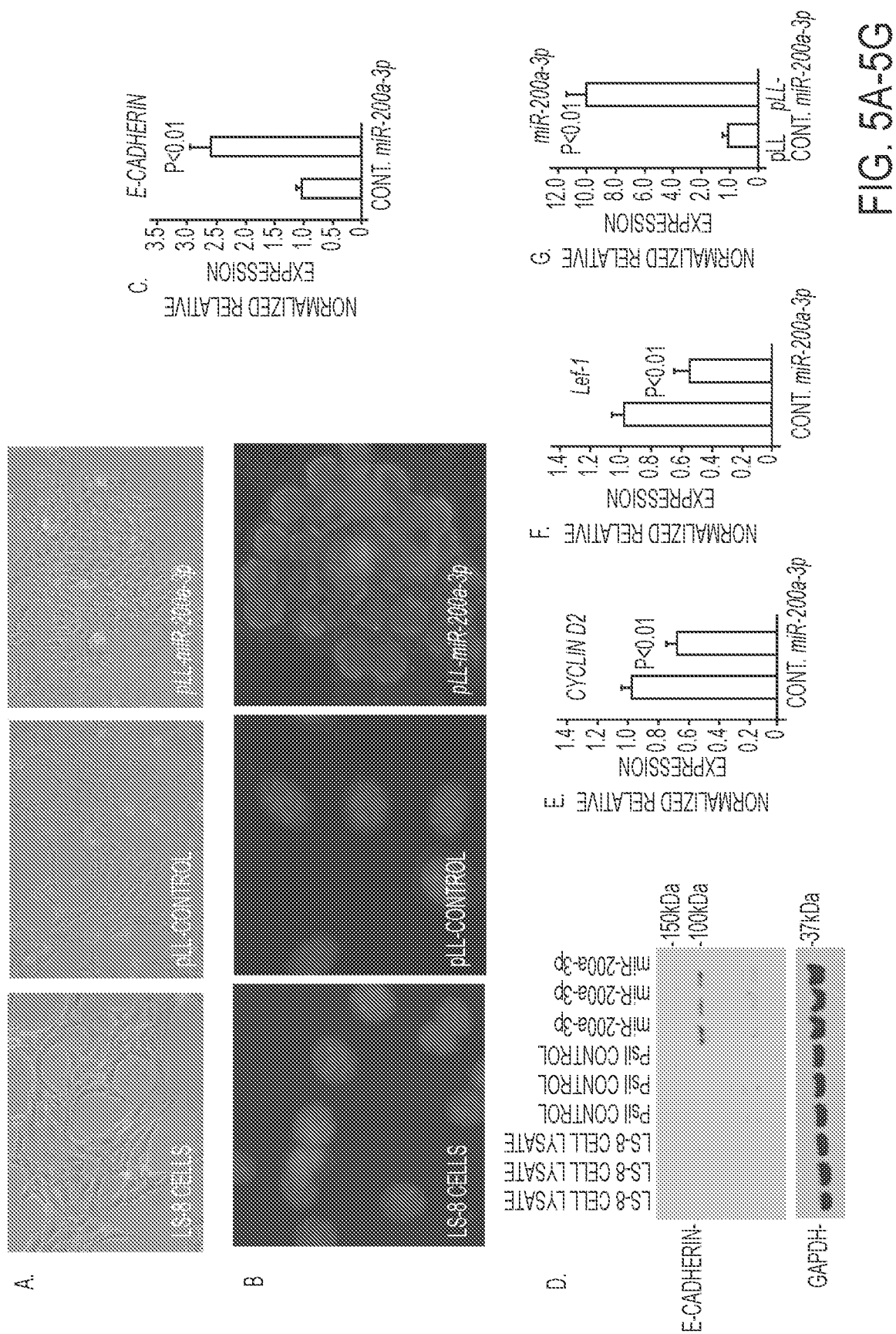
FIGS. 5A-5G. Effect of miR-200a-3p expression in LS-8 cells. A) Morphology change of LS-8 cells transduced with pLL-control and pLL-miR-200a lentivirus constructs. B) E-cadherin staining (green fluorescence) of LS-8, pLL control and pLL-miR-200a transduced cells. DAPI staining used to detect nuclei. C, D) Quantitation by Real time PCR and Western blot of E-cadherin in LS-8 cells transfected with pLL control vector and PLL-miR-200a, respectively. E, F) Quantitation by Real time PCR of Cyclin D2 and Lef-1 in LS-8 cells transfected with pLL control vector and PLL-miR-200a, respectively. G) As a control miR-200a expression was increased in pLL-miR-200a-3p transduced LS-8 cells.

LS-8 cells transduced with lentiviral scrambled or miR-200a-3p constructs were assayed for gene expression and cell morphology changes after two weeks in culture. The LS-8 cells grow similar to fibroblast cells in culture (59) and when transduced with scrambled control vector (FIG. 5A). After miR-200a transduction (pLL-miR-200a) these cells form clusters of cells that more closely resemble epithelial cells (FIG. 5A). Immunocytochemistry (ICC) using an E-cadherin antibody showed increased E-cadherin expression in miR-200a transduced cells (FIG. 5B). Gene expression analyses of the miR-200a-3p transduced LS-8 cells showed increased E-cadherin (both transcripts and protein, FIGS. 5C and D) and miR-200a expression and decreased Cyclin D2 and Lef-1 expression compared to scrambled control cells (FIG. 5E-G).

Figures 6A, 6B, 6C, 6D, 6E, 6F:
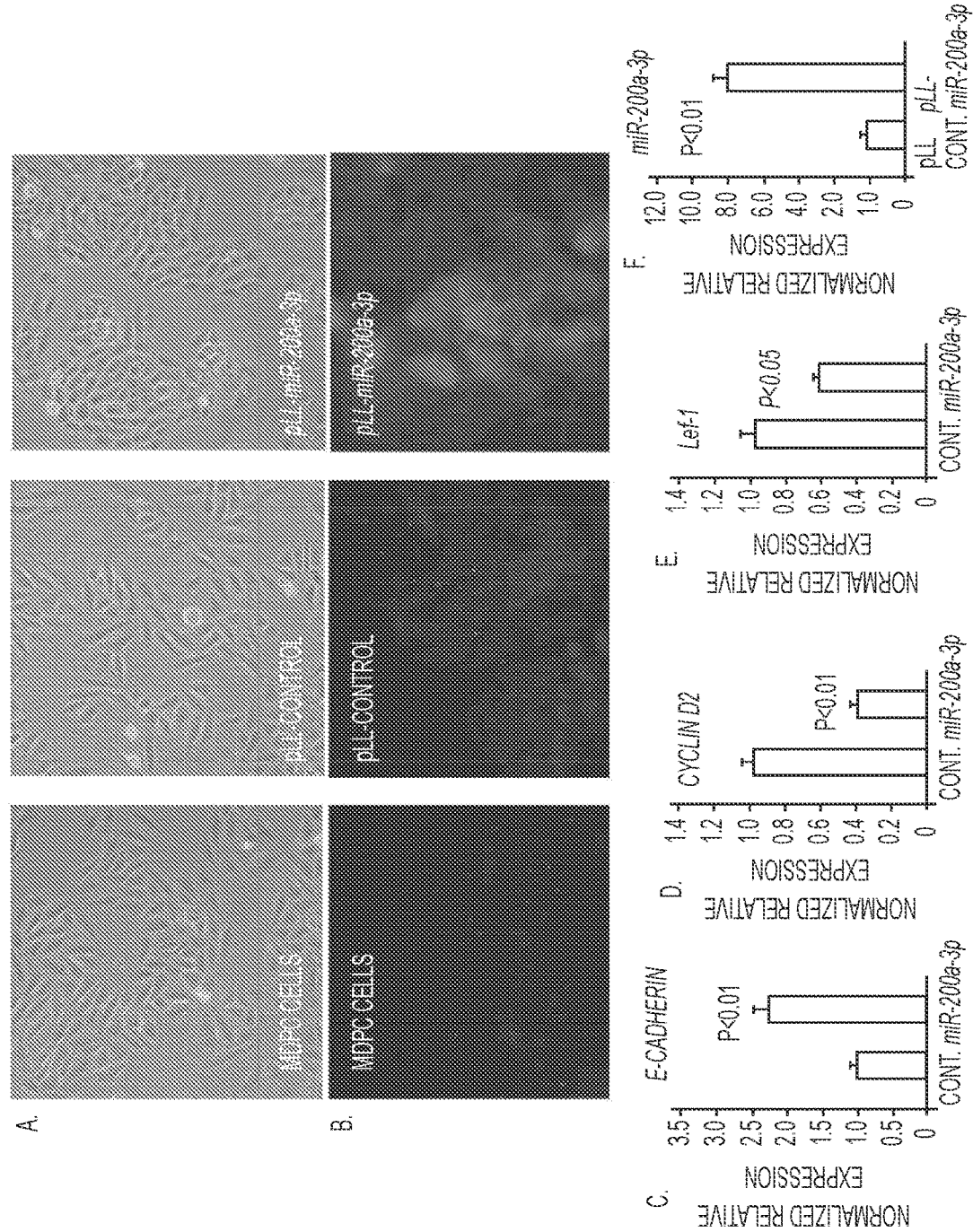
FIGS. 6A-6F. Effect of miR-200a-3p expression in MDPC cells. A) Morphology change of MDPC cells transduced with pLL-control and pLL-miR-200a-3p. B) E-cadherin staining (green fluorescence) of MDPC, pLL control and pLL-miR-200a transduced cells. C-E) Quantitation by Real time PCR of E-cadherin, Cyclin D2 and Lef-1 in MDPC cells transduced with pLL control vector or PLL-miR-200a. F) As a control miR-200a expression was increased in pLL-miR-200a-3p transduced MDPC cells.

The MDPC odontoblast mesenchyme cells (60) were also transduced with scrambled and miR-200a-3p lentiviral constructs and the cells expressing miR-200a-3p showed an epithelial cell morphology (FIG. 6A). The MDPC cells transduced with miR-200a-3p expressed high levels of E-cadherin in culture (FIG. 6B). The transduced MDPC cells have increased E-cadherin and miR-200a-3p expression and decreased Cyclin D2 and Lef-1 expression similar to the miR-200a transduced LS-8 cells (FIG. 6C-F). Interestingly, miR-200a-3p over-expression alone was not sufficient to induce a GRN associated with dental epithelial cells (data not shown). Bioinformatics analyses of both LS-8 and MDPC cells transformed with miR-200a did not activate the dental epithelial cell program identified in mouse dental epithelial tissue.

Several combinations of transcription factors and miRs were analyzed for their effect to reprogram these cells. However, Pitx2 and miR-200a were the best candidates. First, both cell types were transduced with Pitx2 and cells were treated with blastomycin to select stable transduced cells. After 4 weeks the cells were transduced with miR-200a that express GFP and stable cells were initially selected using blastomycin treatment and after culture for one week the cells were FACS sorted using GFP as the marker. Two weeks later the cells were analyzed for morphology and gene expression.

Figure 7A:
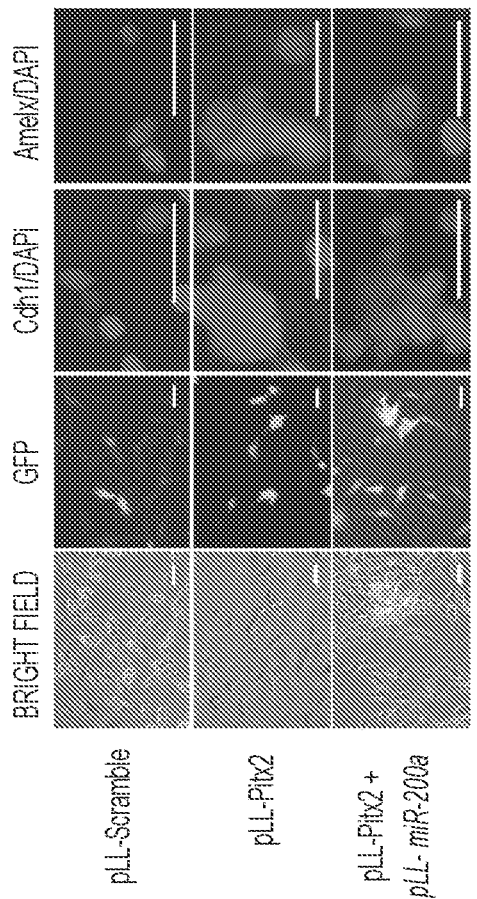
FIGS. 7A-7E. Reprogrammed LS-8 oral epithelial cells express amelogenin and dental epithelial factors. A) LS-8 oral epithelial cells are transduced with pLL-Pitx2 and a combination of pLL-Pitx2 and pLL-miR-200a or lentiviral vector expressing a pLL-scrambled RNA control. Cells were FAC sorted and GFP and immunofluorescence microscopy analysis of changes in the expression levels of Cdh1 and Amelx were observed after eight weeks. Pitx2 transduced cells express low levels of E-cadherin (Cdh1) and amelogenin (Amelx). Pitx2 and miR-200a transduced cells express both Cdh1 and Amelx and form tight junctions between cells. GFP expression shows the cells were transduced with the lentiviral vector. B) RNA-seq analysis of gene expression in response to Pitx2-miR-200a overexpression in LS-8 cells. Significantly up- and down-regulated genes that have at least 2 fold of expression level change were labeled red and blue, respectively. All expression levels were estimated by FPKM. C) Heatmap showing the expression dynamics of selected epithelial-mesenchyme transition (EMT) genes upon Pitx2-miR-200a over-expression. Epithelial specific and mesenchymal specific genes were hierarchically clustered, respectively. D) Real time PCR of selected transcription factors associated with dental epithelial proliferation and differentiation. Endogenous Sox2, Lef-1 and Nanog were increased in the Pitx2-miR-200a transduced LS-8 cells. Pitx2 was overexpressed as expected (Pitx2 cDNA is not regulated by miR-200a). Pou5fl (Oct4) was not significantly changed. N>3, *p<0.05, **p<0.01. E) Gene Ontology (GO) analysis significantly up- and down-regulated genes. Top enriched GO terms (−log 2 p value>10) are highlighted for both up-regulated (red) and down-regulated (blue) genes that are related to EMT and morphogenic functions.
Figure 7B:
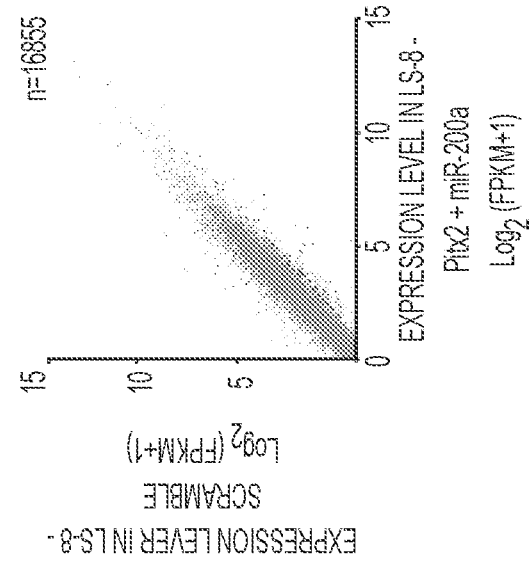
Figure 7C:
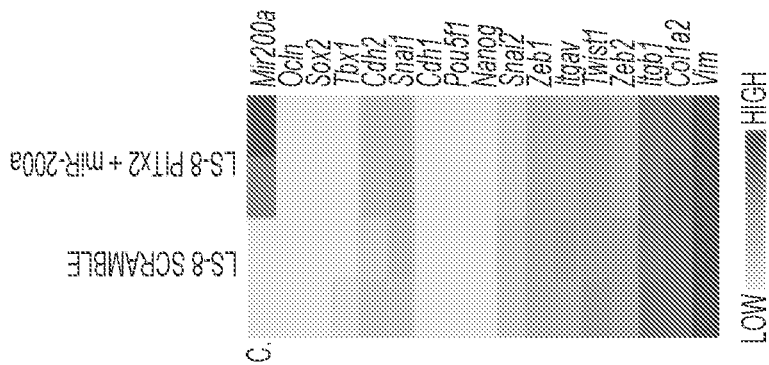
Figures 7D, 7E:
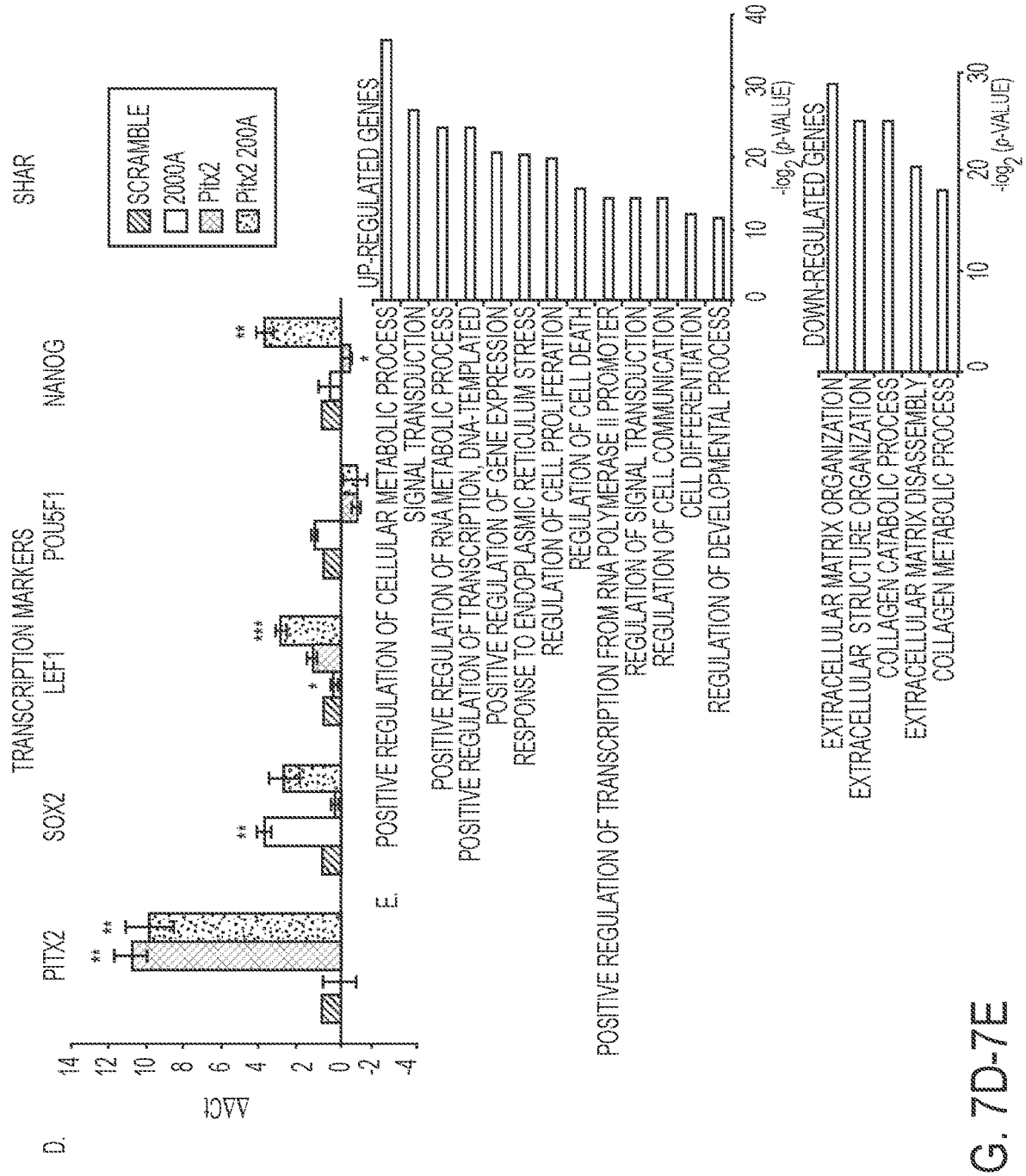
Figures 8A, 8B:
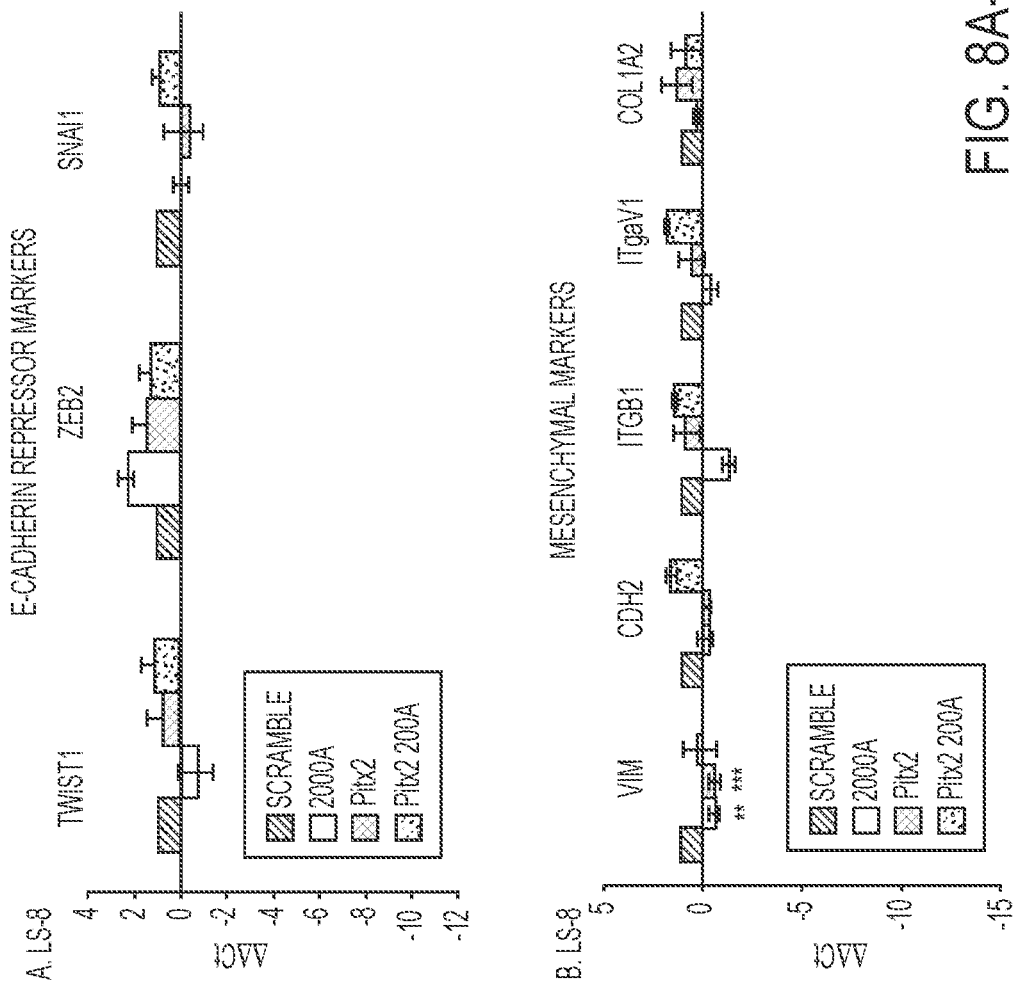
FIGS. 8A-8B. FACS sorted transduced LS-8 cells were analyzed for specific gene expression. A) The E-cadherin repressor genes, Twist1, Zeb2 and Snail1 were all increased in the Pitx2-miR-200a transduced cells. N=3. B) Mesenchymal markers were not increased above scrambled control cells and the expression levels were low (>Ct 30). N=3.

E-cadherin and amelogenin are well-known dental epithelial differentiation markers and characterize fully differentiated ameloblast cells (71-76). LS-8 cells after Pitx2 transduction express amelogenin (Amelx) but not E-cadherin (CDH1) (FIG. 7A), it has been shown that increased Lef-1 expression reduces E-cadherin expression (70). However, after transduction with Pitx2 and miR-200a both E-cadherin and amelogenin were expressed (FIG. 7A, bottom panel). Gene expression involved in MET in the Pitx2 and miR-200a transduced LS-8 cells was analyzed by RNA-seq. and confirmed by qPCR (FIG. 7B-E). Real time PCR confirmed the up regulation of Pitx2, Sox2, Lef-1 and Nanog in converted LS-8 cells (FIG. 7D), and from the RNA-seq. experiments genes that regulate transcription and signal transduction (FIG. 7E). Conversely, in LS-8 reprogrammed cells E-cadherin repression markers and mesenchymal markers were not significantly changed compared to scrambled control cells (FIG. 8A, B). RNA-seq. identified multiple genes associated with collagen and extracellular matrix processes that were down regulated (FIG. 7E). These data are consistent with conversion of LS-8 oral epithelial cells to dental epithelial cells. A selected list of dental epithelial (pre-ameloblast and ameloblast) transcription factors and other genes are listed in Table 1. These genes are highly expressed and appear to be signature genes for differentiated dental epithelium. We compare the converted LS-8 oral epithelial cells and MDPC cells to this signature. Most of these factors are expressed in the oral epithelial cells and we find modest increases in their expression after Pitx2 and miR-200a expression. However, the converted MDPC dental mesenchyme cells demonstrate large increases in the expression of these dental epithelial genes.

Figures 9A, 9B, 9C:
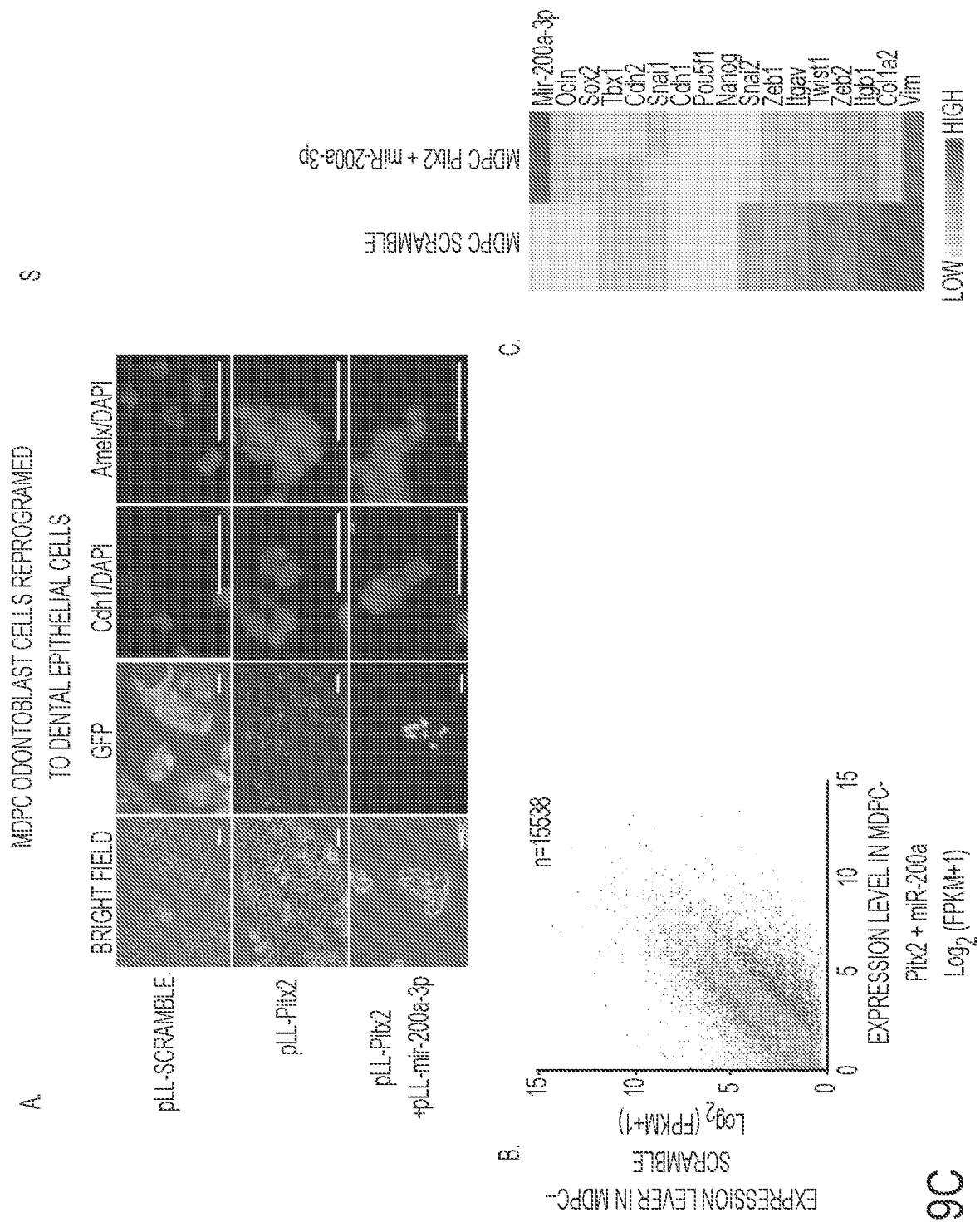

MDPC mesenchyme cells after miR-200a transduction express E-cadherin (CDH1) but not amelogenin, however after Pitx2 transduction these cells express amelogenin but not E-cadherin (FIG. 9A). Transduction with Pitx2 and miR-200a stimulated both E-cadherin and amelogenin expression (FIG. 9A). Gene expression involved in MET in the Pitx2 and miR-200a transduced MDPC cells was analyzed by RNA-seq. and confirmed by qPCR (FIG. 9B-E). Real time PCR confirmed the up regulation of Pitx2, Sox2 and Lef-1 in converted MDPC cells and from the RNA-seq. experiments genes that regulate transcription and signal transduction (FIG. 9D, E). As expected, in MDPC converted cells E-cadherin expression was up-regulated and mesenchymal markers were all down-regulated (FIG. 10A, B). The significant gene expression changes demonstrate that these reprogrammed MDPC cells have undergone an epithelial conversion to a dental epithelial cell fate. RNA-seq. identified multiple genes that were down regulated and associated with collagen and extracellular matrix processes indicative of mesenchyme cells (FIG. 9E).

Discussion

In the recent past there has been an explosion of studies using dental stem cells and isolated dental epithelial-mesenchyme interactions to generate epithelial cells and tissue for tooth bioengineering and regeneration (1,59,74,77-89). Many of the genes required for epithelial cell proliferation and differentiation during tooth organogenesis and regeneration have been identified and are being used in research to make teeth (33-35,90). There are an abundance of studies using dental stem cells, mesenchyme stem cells, bone marrow stem cells and epithelial-mesenchyme interactions to differentiate epithelial cells capable of regenerating dental epithelium and dental structures (over 100 manuscripts published). A common theme in these studies relies on the isolation of dental progenitor or stem cells to generate competent differentiated dental epithelial cells. These procedures are intrusive and provide limited amounts of material. A procedure to convert easily obtained oral epithelial cells or dental mesenchyme cells from patients would greatly facilitate tooth and tissue regeneration.

miRs have been identified as key regulators of progenitor cell differentiation and modulators of cell fate decisions (21,31,44,45,91). miRs regulate the fate of stem cells in many different tissues and organs through the specification or differentiation of cell types. miRs can target cell cycle regulators, promote differentiation by inactivating transcriptional repressors, integrate with transcriptional and signaling networks in bone formation, muscle differentiation, neurogenesis, and tooth and craniofacial morphogenesis (21,31,44,45,92). The use of miRs in cell reprogramming is a new field of research that has great promise for tooth regeneration.

Wnt/β-catenin signaling, Tcf/Lef-1 and Sox factors control stem cell renewal and differentiation in many tissues and organs, including teeth (14,17,93-95). Lef-1 is required for early tooth formation and cell proliferation (18,19). Pitx2 also controls dental progenitor cell proliferation and differentiation (31,96). Pitx2 physically interacts with β-catenin to activate Lef-1 expression and miR-200c expression to inhibit Noggin and activate BMP to allow for dental epithelial cell differentiation (9,10,31). This unique signaling network and GRN suggested that these factors might regulate dental epithelial cell fate. The bioinformatics analyses described herein demonstrate that Wnt signaling-associated factors involved in odontogenesis are increased in Pitx2-miR-200 converted cells including Fzd9, Fzd8, Wnt 11, Fzd6. Furthermore, we constructed a list of highly expressed factors expressed in P0 mouse dental epithelium, which we use as a signature to designate dental epithelium (Table 1). This signature only denotes the highly expressed genes and excludes other genes (not highly expressed) that are also associated with dental epithelium. The converted dental mesenchyme to dental epithelium cells all highly express these factors. Interestingly, the oral epithelial cells express these factors and thus are only moderately increased in the converted dental epithelial cells.

As described herein, a new GRN has been identified, where Pitx2 activates miR-200a expression and this miR then feeds back to modulate Pitx2 expression as dental progenitor cells differentiate. miR-200a represses β-catenin expression and this GRN then indirectly modulates Lef-1 expression. miR-200a is a regulator of dental epithelial progenitor cell differentiation. However, miR-200a can also specify epithelial cell fates by repressing Zeb expression to allow for E-cadherin expression. This unique molecular mechanism guides tissue morphogenesis. As described herein, this process was hijacked by over-expressing Pitx2 as a cDNA (not regulated by miR-200a) to activate the dental epithelial GRN, including amelogenin and using miR-200a over-expression to establish the epithelial cell program.

Studies based in our laboratory with the current findings establish a new method to reprogram both oral epithelial and dental mesenchyme cells to a dental epithelial cell fate (FIG. 11). Because functional dental epithelial cell cultures are a limiting resource in tissue engineering this technique should have great potential to help produce epithelial tissues for tooth and craniofacial repair and regeneration. Human oral epithelium can be obtained from patients and reprogrammed to yield sufficient amounts of dental epithelium for tooth replacement. We are currently using these findings to initiate tooth regeneration.

REFERENCES

1. Harada, H., Kettumen, P., Jung, H.-S., Mustonen, T., Wang, Y. A., and Thesleff, I. (1999) Localization of Putative Stem Cells in Dental Epithelium and Their Association with Notch and FGF Signaling. *J. Cell Biol.* 147, 105-120
2. Tummers, M., and Thesleff, I. (2003) Root or crown: a developmental choice orchestrated by the differential regulation of the epithelial stem cell niche in the tooth of two rodent species. *Development* 130, 1049-1057
3. Tummers, M., and Thesleff, I. (2008) Observations on continuously growing roots of the sloth and the K14-Eda transgenic mice indicate that epithelial stem cells can give rise to both the ameloblast and root epithelium cell lineage creating distinct tooth patterns. *Evol Dev* 10, 187-195
4. Wang, X.-P., Suomalainen, M., Felszeghy, S., Zelarayan, L. C., Alonso, M. T., Plikus, M. V., Maas, R. L., Chuong, C.-M., Schimmang, T., and Thesleff, I. (2007) An Integrated Gene Regulatory Network Controls Stem Cell Proliferation in Teeth. *Plos Biol.* 5, e159
5. Neubuser, A., Peters, H., Balling, R., and Martin, G. R. (1997) Antagonistic interactions between FGF and BMP signaling pathways: a mechanism for positioning the sites of tooth formation. *Cell* 90, 247-255
6. St.Amand, T. R., Zhang, Y., Semina, E V., Zhao, X., Hu, Y., Nguyen, L., Murray, J. C., and Chen, Y. (2000) Antagonistic Signals between BMP4 and FGF8 Define the Expression of Pitx1 and Pitx2 in Mouse Tooth-Forming Anlage. *Dev. Biol.* 217, 323-332
7. Lin, C. R., Kioussi, C., O'Connell, S., Briata, P., Szeto, D., Liu, F., Izpisua-Belmonte, J. C., and Rosenfeld, M. G. (1999) Pitx2 regulates lung asymmetry, cardiac positioning and pituitary and tooth morphogenesis. *Nature* 401, 279-282
8. Logan, C. Y., and Nusse, R. (2004) The Wnt signaling pathway in development and disease. *Annual review of cell and developmental biology* 20, 781-810
9. Vadlamudi, U., Espinoza, H. M., Ganga, M., Martin, D. M., Liu, X., Engelhardt, J. F., and Amendt, B. A. (2005) PITX2, β-catenin, and LEF-1 Interact to Synergistically Regulate the LEF-1 promoter. *J. Cell Sci.* 118, 1129-1137
10. Amen, M., Liu, X., Vadlamudi, U., Elizondo, G., Diamond, E., Engelhardt, J. F., and Amendt, B. A. (2007) PITX2 and β-catenin Interactions Regulate Lef-1 Isoform Expression. *Mol. Cell. Biol.* 27, 7560-7573.
11. Chu, K. B., Douglas, K. R., Potok, M. A., Liang, H., Jones, S. N., and Camper, S. A. (2004) WNT5A signaling affects pituitary gland shape. *Mech. Dev.* 121, 183-194
12. Gat, U., DasGupta, R., Degenstein, L., and Fuchs, E. (1998) De Novo hair follicle morphogenesis and hair tumors in mice expressing a truncated beta-catenin in skin. *Cell* 95, 605-614
13. Hogan, B. L. (1999) Morphogenesis. *Cell* 96, 225-233
14. Liu, F., Chu, E. Y., Watt, B., Zhang, Y., Gallant, N. M., Andl, T., Yang, S. H., Lu, M.-M., Piccolo, S., Schmidt-Ullrich, R., Taketo, M. M., Morrisey, E. E., Atit, R., Dlugosz, A. A., and Millar, S. E. (2008) Wnt/beta-catenin signaling directs multiple stages of tooth morphogenesis. *Dev. Biol.* 313, 210-224
15. Noramly, S., Freeman, A., and Morgan, B. A. (1999) beta-catenin signaling can initiate feather bud development. *Development* 126, 3509-3521
16. Thesleff, I., and Nieminen, P. (1996a) Tooth morphogenesis and cell differentiation. *Cur. Opin. Cell Biol.* 8, 844-850
17. Järvinen, E., Salazar-Ciudad, I., Birchmeier, W., Taketo, M., M., Jernvall, J., and Thesleff, I. (2006) Continuous tooth generation in mouse is induced by activated epithelial Wnt/beta-catenin signaling. *Proc. Natl. Acad. Sci. USA* 103, 18627-18632
18. Kratochwil, K., Dull, M., Farinas, I., Galceran, J., and Grosschedl, R. (1996) Lef1 expression is activated by BMP-4 and regulates inductive tissue interactions in tooth and hair development. *Genes Dev.* 10, 1382-1394
19. Sasaki, T., Ito, Y., Xu, X., Han, J., Bringas, J., P., Maeda, T., Slavkin, H. C., Grosschedl, R., and Chai, Y. (2005) LEF1 is a critical epithelial survival factor during tooth morphogenesis. *Dev. Biol.* 278, 130-143
20. Bartel, D. P. (2004) MicroRNAs: genomics, biogenesis, mechanism, and function. *Cell* 116, 281-297
21. Cao, H., Wang, J., Li, X., Florez, S., Huang, Z., Venugopalan, S. R., Elangovan, S., Skobe, Z., Margolis, H. C., Martin, J. F., and Amendt, B. A. (2010) MicroRNAs play a critical role in tooth development. *J Dent Res* 89, 779-784
22. Michon, F., Tummers, M., Kyyronen, M., Frilander, M. J., and Thesleff, I. (2010) Tooth morphogenesis and ameloblast differentiation are regulated by micro-RNAs. *Dev Biol* 340, 355-368
23. Mongroo, P. S., and Rustgi, A. K. (2010) The role of the miR-200 family in epithelial-mesenchymal transition. *Cancer Biology & Therapy* 10, 219-222
24. Brabletz, S., Bajdak, K., Meidhof, S., Burk, U., Niedermann, G., Firat, E., Wellner, U., Dimmler, A., Faller, G., Schubert, J., and Brabletz, T. (2011) The ZEB1/miR-200 feedback loop controls Notch signalling in cancer cells. *EMBO J* 30, 770-782
25. Wellner, U., Schubert, J., Burk, U. C., Schmalhofer, O., Zhu, F., Sonntag, A., Waldvogel, B., Vannier, C., Darling, D., Hausen, A., Brunton, V. G., Morton, J., Sansom, O., Schuler, J., Stemmler, M. P., Herzberger, C., Hopt, U., Keck, T., Brabletz, S., and Brabletz, T. (2009) The EMT-activator ZEB1 promotes tumorigenicity by repressing sternness-inhibiting microRNAs. *Nat Cell Biol* 11, 1487-1495
26. Korpal, M., Lee, E. S., Hu, G., and Kang, Y. (2008) The miR-200 Family Inhibits Epithelial-Mesenchymal Transition and Cancer Cell Migration by Direct Targeting of E-cadherin Transcriptional Repressors ZEB1 and ZEB2. *J Biol Chem* 283, 14910-14914
27. Gregory, P. A., Bert, A. G., Paterson, E. I., Barry, S. C., Tsykin, A., Farshid, G., Vadas, M. A., Khew-Goodall, Y., and Goodall, G. J. (2008) The miR-200 family and miR-205 regulate epithelial to mesenchymal transition by targeting ZEB1 and SIP1. *Nat Cell Biol.* 10, 593-601

28. Burk, U., Schubert, J., Wellner, U., Schmalhofer, O., Vincan, E., Spaderna, S., and Brabletz, T. (2008) A reciprocal repression between ZEB1 and members of the miR-200 family promotes EMT and invasion in cancer cells. *EMBO Reports* 9, 582-589
29. Brabletz, S., and Brabletz, T. (2010) The ZEB/miR-200 feedback loop—a motor of cellular plasticity in development and cancer? *EMBO Reports* 11, 670-677
30. Jheon, A. H., Li, C.-Y., Wen, T., Michon, F., and Klein, O. D. (2011) Expression of MicroRNAs in the Stem Cell Niche of the Adult Mouse Incisor. *Plos ONE* 6, e24536
31. Cao, H., Jheon, A., Li, X., Sun, Z., Wang, J., Florez, S., Zhang, Z., McManus, M. T., Klein, O. D., and Amendt, B. A. (2013) The Pitx2:miR-200c/141:noggin pathway regulates Bmp signaling and ameloblast differentiation. *Development* 140, 3348-3359
32. Morotomi, T., Kawano, S., Toyono, T., Kitamura, C., Terashita, M., Uchida, T., Toyoshima, K., and Harada, H. (2005) In vitro differentiation of dental epithelial progenitor cells through epithelial-mesenchymal interactions. *Arch. Oral Biol.* 50, 695-705
33. Tucker, A., and Sharpe, P. (2004) The cutting-edge of mammalian development; how the embryo makes teeth. *Nat. Rev. Genet.* 5, 499-508
34. Zhang, Y. D., Chen, Z., Song, Y. Q., Liu, C., and Chen, Y. (2005) Making a tooth: growth factors, transcription factors and stem cells. *Cell Res.* 15, 301-316
35. Ikeda, E., Morita, R., Nakao, K., Ishida, K., Nakamura, T., Takano-Yamamoto, T., Ogawa, M., Mizuno, M., Kasugai, S., and Tsuji, T. (2009) Fully functional bioengineered tooth replacement as an organ replacement therapy. *Proc. Nat. Acad. Sci. USA* 106, 13475-13480
36. Sharpe, P. T., and Young, C. S. (2005) Test-tube teeth. *Sci. Am.* 293, 34-41
37. Yen, A. H., and Sharpe, P. T. (2006) Regeneration of teeth using stem cell-based tissue engineering. *Expert Opin. Biol. Ther.* 6, 9-16
38. Shi, S., Bartold, P.-M., Miura, M., Seo, B.-M., Robey, P. G., and Gronthos, S. (2005) The efficacy of mesenchymal stem cells to regenerate and repair dental structures. *Orthod. Craniofacial Res.* 8, 191-199
39. Menicanin, D., Mrozik, K. M., Wada, N., Marino, V., Shi, S., Bartold, P.-M., and Gronthos, S. (2014) Periodontal-Ligament-Derived Stem Cells Exhibit the Capacity for Long-Term Survival, Self-Renewal, and Regeneration of Multiple Tissue Types in Vivo. *Stem Cells Dev.* 23, 1001-1011
40. Menicanin, D., Bartold, P.-M., Zannettino, A. C., and Gronthos, S. (2010) Identification of a common gene expression signature associated with immature clonal mesenchymal cell populations derived from bone marrow and dental tissues. *Stem Cells Dev.* 19, 1501-1510
41. Gronthos, S., Arthur, A., Bartold, P.-M., and Shi, S. (2011) A method to isolate and culture expand human dental pulp stem cells. *Methods Mol. Biol.* 698, 107-121
42. Hynes, K., Menicanin, D., Mrozik, K., Gronthos, S., and Bartold, P.-M. (2014) Generation of Functional Mesenchymal Stem Cells from Different Induced Pluripotent Stem Cell Lines. *Stem Cells Dev.* 23, 1084-1096
43. Takahashi, K., and Yamanaka, S. (2006) Induction of Pluripotent Stem Cells from Mouse Embryonic and Adult Fibroblast Cultures by Defined Factors. *Cell* 126, 663
44. Ivey, K. N., and Srivastava, D. (2010) MicroRNAs as Regulators of Differentiation and Cell Fate Decisions. *Cell Stem Cell* 7, 36-41
45. Martinez N. J., and Gregory, R. I. (2010) MicroRNA gene regulatory pathways in the establishment and maintenance of ESC identity. *Cell Stem Cell* 7, 31-35
46. Amendt, B. A., Sutherland, L. B., and Russo, A. F. (1999) Multifunctional Role of the Pitx2 Homeodomain Protein C-Terminal Tail. *Mol. Cel. Biol.* 19, 7001-7010
47. Cox, C. J., Espinoza, H. M., McWilliams, B., Chappell, K., Morton, L., Hjalt, T. A., Semina, E. V., and Amendt, B. A. (2002) Differential Regulation of Gene Expression by PITX2 Isoforms. *J. Biol. Chem.* 277, 25001-25010
48. Amendt, B. A., Sutherland, L. B., Semina, E., and Russo, A. F. (1998) The Molecular Basis of Rieger Syndrome: Analysis of Pitx2 Homeodomain Protein Activities. *J. Biol. Chem.* 273, 20066-20072
49. Filali, M., Cheng, N., Abbott, D., Leontiev, V., and Engelhardt, J. F. (2002) Wnt-3A/β-catenin Signaling Induces Transcription from the LEF-1 Promoter. *J. Biol. Chem.* 277, 33398-33410
50. Zhang, Z., Wlodarczyk, B. J., Niederreither, K., Venugopalan, S., Florez, S., Finnell, R. H., and Amendt, B. A. (2011) Fuz Regulates Craniofacial Development Through Tissue Specific Responses to Signaling Factors. *PLoS ONE* 6: e24608
51. Cao, H., Florez, S., Amen, M., Huynh, T., Skobe, Z., Baldini, A., and Amendt, B. A. (2010) Tbx1 regulates progenitor cell proliferation in the dental epithelium by modulating Pitx2 activation of p21. *Dev Biol* 347, 289-300
52. Amen, M., Espinoza, H. M., Cox, C., Liang, X., Wang, J., Link, T. M., Brennan, R. G., Martin, J. F., and Amendt, B. A. (2008) Chromatin-associated HMG-17 is a major regulator of homeodomain transcription factor activity modulated by Wnt/beta-catenin signaling. *Nuc. Acids Res.* 36, 462-476
53. Cui, X.-M., Shiomi, N., Chen, J., Saito, T., Yamamoto, T., Ito, Y., Bringas, P., Chai, Y., and Shuler, C. F. (2005) Overexpression of Smad2 in Tgf-b3-null mutant mice rescues cleft palate. *Dev. Biol.* 278, 193-202
54. Venugopalan, S. R., Amen, M. A., Wang, J., Wong, L., Cavender, A. C., D'Souza, R. N., Akerlund, M., Brody, S. L., Hjalt, T. A., and Amendt, B. A. (2008) Novel expression and transcriptional regulation of FoxJ1 during orofacial morphogenesis. *Hum. Mol. Genet.* 17, 3643-3654
55. Chavez, M. G., Yu, W., Biehs, B., Harada, H., Snead, M. L., Lee, J. S., Desai, T. A., and Klein, O. D. (2013) Characterization of dental epithelial stem cells from the mouse incisor with two-dimensional and three-dimensional platforms. *Tissue Eng Part C Methods* 19, 15-24
56. Chavez, M. G., Hu, J., Seidel, K., Li, C., Jheon, A., Naveau, A., Horst, O., and Klein, O. D. (2014) Isolation and culture of dental epithelial stem cells from the adult mouse incisor. *J. Vis. Exp.* 87, doi: 10.3791/51266
57. Hu, K.-H. J., Mushegyan, V., and Klein, O. D. (2014) On the cutting edge of organ renewal: Identification, regulation, and evolution of incisor stem cells. *Genesis* 52, 79-92
58. Zhang, Z., Florez, S., Gutierrez-Hartmann, A., Martin, J. F., and Amendt, B. A. (2010) MicroRNAs regulate pituitary development, and microRNA 26b specifically targets lymphoid enhancer factor 1 (Lef-1), which modulates pituitary transcription factor 1 (Pit-1) expression. *J Biol Chem* 285, 34718-34728
59. Chen, L. S., Couwenhoven, R. I., Hsu, D., Luo, W., and Snead, M. L. (1992) Maintenance of Amelogenin Gene Expression by Transformed Epithelial Cells of Mouse Enamel Organ. *Archs oral Biol.* 37, 771-778

60. Hanks, C. T., Fang, D., Sun, Z., Edwards, C. A., and Butler, W. T. (1998) Dentin-specific proteins in MDPC-23 cell line. *Eur. J. Oral Sci.* 106, 260-266
61. Goecks, J., Nekrutenko, A., Taylor, J., and Team, T. G. (2010) Galaxy: a comprehensive approach for supporting accessible, reproducible, and transparent computational research in the life sciences. *Genome Biol.* 11, R86
62. Blankenberg, D., Von Kuster, G., Coraor, N., Ananda, G., Lazarus, R., Mangan, M., Nekrutenko, A., and Taylor, J. (2010) "Galaxy: a web-based genome analysis tool for experimentalists". *Current Protocols Molecular Biology* Ch. 19, Unit 19.10.1-21
63. Giardine, B., Riemer, C., Hardison, R. C., Burhans, R., Elnitski, L., Shah, P., Zhang, Y., Blankenberg, D., Albert, I., Taylor, J., Miller, W., Kent, W. J., and Nekrutenko, A. (2005) "Galaxy: a platform for interactive large-scale genome analysis.". *Genome Res* 15, 1451-1455
64. Trapnell, C., Roberts, A., Goff, L., Pertea, G., Kim, D., Kelley, D. R., Pimentel, H., Salzberg, S. L., Rinn, J. L., and Pachter, L. (2012) Differential gene and transcript expression analysis of RNA-seq experiments with TopHat and Cufflinks. *Nat. Protoc.* 7, 562-578
65. Saldanha, A. J. (2004) Java Treeview—extensible visualization of microarray data. *Bioinformatics* 20, 3246-3248
66. de Hoon, M. J., Imoto, S., Nolan, J., and Miyano, S. (2004) Open source clustering software. *Bioinformatics* 20, 1453-1454
67. Mucchielli, M.-L., Mitsiadis, T. A., Raffo, S., Brunet, J.-F., Proust, J.-P., and Goridis, C. (1997) Mouse Otlx2/RIEG Expression in the Odontogenic Epithelium Precedes Tooth Initiation and Requires Mesenchyme-Derived Signals for Its Maintenance. *Dev. Biol.* 189, 275-284
68. Hjalt, T. A., Semina, E. V., Amendt, B. A., and Murray, J. C. (2000) The Pitx2 Protein in Mouse Development. *Dev. Dyn.* 218, 195-200
69. Xia, H., Cheung, W. K. C., Sze, J., Lu, G., Jiang, S., Yao, H., Bian, X.-W., Poon, W. S., Kung, H.-F., and Lin, M. C. (2010) miR-200a Regulates Epithelial-Mesenchymal to Stem-like Transition via ZEB2 and β-Catenin Signaling. *J Biol Chem* 285, 36995-37004
70. Stockinger, A., Eger, A., Wolf, J., Beug, H., and Foisner, R. (2001) E-cadherin regulates cell growth by modulating proliferation-dependent β-catenin transcriptional activity. *J. Cell Biol.* 154, 1185-1196
71. Chen, S., Lewallen, M., and Xie, T. (2013) Adhesion in the stem cell niche: biological roles and regulation. *Development* 140, 255-265
72. Li, C. Y., Cha, W. H., Luder, H. U., Charles, R. P., McMahon, M., Mitsiadis, T. A., and Klein, O. D. (2012) E-cadherin regulates the behavior and fate of epithelial stem cells and their progeny in the mouse incisor. *Developmental Biology* 366, 357-366
73. Karpowicz, P., Willaime-Morawek, S., Balenci, L., DeVeale, B., Inoue, T., and van der Kooy, D. (2009) E-Cadherin regulates neural stem cell self-renewal. *J. Neurosci.* 29, 3885-3896
74. DenBesten, P. K., Machule, D., Zhang, Y., Yan, Q., and Li, W. (2005) Characterization of human primary enamel organ epithelial cells in vitro. *Arch. Oral Biol.* 50, 689-694
75. Nakahori, Y., Takenaka, O., and Nakagome, Y. (1991) A human X-Y homologous region encodes "amelogenin". *Genomics* 9, 264-269
76. Snead, M. L., Lau, E. C., Zeichner-David, M., Fincham, A. G., Woo, S. L., and Slavkin, H. C. (1985) DNA sequence for cloned cDNA for murine amelogenin reveal the amino acid sequence for enamel-specific protein. *Biochem Biophys Res Commun.* 129, 812-818
77. Peters, H., and Balling, R. (1999) Teeth, where and how to make them. *TIG* 15, 59-64
78. Jernvall, J., and Thesleff, I. (2000) Reiterative signaling and patterning during mammalian tooth morphogenesis. *Mech. Dev.* 92, 19-29
79. Zeichner-David, M., Diekwisch, T., Fincham, A., Lau, E., MacDougall, M., Moradian-Oldak, J., Simmer, J., Snead, M., and Slavkin, H. C. (1995) Control of ameloblast differentiation. *Int. J. Dev. Biol.* 39, 69-92
80. Mustonen, T., Tummers, M., Mikami, T., Itoh, N., Zhang, N., Gridley, T., and Thesleff, I. (2002) Lunatic fringe, FGF, and BMP regulate the Notch pathway during epithelial morphogenesis of teeth. *Dev Biol* 248, 281-293
81. Limeback, H. (1987) Enamel protein and collagen production by cells subcultured from porcine tooth bud explants. *Biochem. Cell Biol.* 65, 698-709
82. Farges, J. C., Couble, M. L., Joffre, A., Hartmann, D. J., and Magloire, H. (1991) Morphological and immunocytochemical characterization of cultured rat incisor cervical epithelial cells. *Arch Oral Biol.* 36, 737-745
83. Tabata, M. J., Matsumura, T., Liu, J. G., Wakisaka, S., and Kurisu, K. (1996) Expression of cytokeratin 14 in ameloblast-lineage cells of the developing tooth of rat, both in vivo and in vitro. *Arch Oral Biol.* 41, 1019-1027
84. Matsumura, T., Tabata, M. J., Wakisaka, S., Sakuda, M., and Kurisu, K. (1998) Ameloblast-lineage cells of rat tooth germs proliferate and scatter in response to hepatocyte growth factor in culture. *Int J Dev Biol* 42, 1137-1142
85. Tabata, M. J., Matsumura, T., Fujii, T., Abe, M., and Kurisu, K. (2003) Fibronectin accelerates the growth and differentiation of ameloblast lineage cells in vitro. *J Histochem. Cytochem.* 51, 1673-1679
86. Kawano, S., Saito, M., Handa, K., Morotomi, T., Toyono, T., Seta, Y., Nakamura, N., Uchida, T., Toyoshima, K., Ohishi, M., and Harada, H. (2004) Characterization of dental epithelial progenitor cells derived from cervical-loop epithelium in a rat lower incisor. *J Dent Res* 83, 129-133
87. Harada, H., Toyono, T., Toyoshima, K., Yamasaki, M., Itoh, N., Kato, S., Sekine, K., and Ohuchi, H. (2002) FGF10 maintains stem cell compartment in developing mouse incisors. *Development* 129, 1533-1541
88. Harada, H., and Ohshima, H. (2004) New perspectives on tooth development and the dental stem cell niche. *Arch. Histol. Cytol.* 67, 1-11
89. Maas, R., and Bei, M. (1997) The genetic control of early tooth development. *Crit. Rev. Oral. Biol. Med.* 8, 4-39
90. Thesleff, I., and Tummers, M. (2009) Tooth organogenesis and regeneration. *The Stem Cell Research Community, StemBook* StemBook, ed
91. Yoo, A. S., Sun, A. X., Li, L., Shchegiovitov, A., Portmann, T., Li, Y., Lee-Meser, C., Dolmetsch, R. E., Tsien, R. W., and Crabtree, G. R. (2011) MicroRNA-mediated conversion of human fibroblasts to neurons. *Nature* 476, 228-231
92. Gay, I., Cavender, A., Peto, D., Sun, Z., Speer, A., Cao, H., and Amendt, B. A. (2013) Differentiation of human dental stem cells reveals a role for microRNA-218.1 *Periodontal Res.* 49, 110-120
93. Cui, L., Guan, Y., Qu, Z., Zhang, J., Liao, B., Ma, B., Qian, J., Li, D., Li, W., Xu, G.-T., and Jin, Y. (2013) WNT signaling determine tumorigenicity and function of ESC-derived retinal progenitors. *J Clin. Invest.* 123, 1647-1661

94. Liu, F., and Millar, S. E. (2010) Wnt/β-catenin signaling in oral tissue development and disease. *J. Dent. Res.* 89, 318-330
95. Bei, M. (2009) Molecular genetics of tooth development. *Curr. Opin. Genet. Dev.* 19, 504-510
96. Liu, W., Selever, J., Lu, M. F., and Martin, J. F. (2003) Genetic dissection of Pitx2 in craniofacial development uncovers new functions in branchial arch morphogenesis, late aspects of tooth morphogenesis and cell migration. *Development* 130, 6375-6385

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

---

What is claimed is:

1. A method of generating a re-programmed differentiated mammalian dental epithelial cell comprising
   (a) transfecting a mammalian oral epithelial cell or a mammalian odontoblast mesenchymal cell via electroporation or Lipofectin with a vector comprising a nucleic acid encoding Pitx2 to form a de-differentiated cell, and
   (b) transfecting the de-differentiated cell via electroporation or Lipofectin with a vector comprising a promoter operably linked to a nucleic acid encoding a miR-200a-3p to form a re-programmed differentiated epithelial cell, and
   (c) culturing the re-programmed differentiated epithelial cell to generate a mammalian dental epithelial cell that expresses amelogenin.

2. The method of claim 1, wherein the promoter is a polII or polIII promoter.

3. The method of claim 1, wherein the promoter comprises at least one of a tissue-specific promoter and an inducible promoter.

4. The method of claim 1, wherein the vector comprising the promoter operably linked to the nucleic acid encoding the miR-200a-3p further comprises a marker gene.

5. The method of claim 1, wherein the vector of step (a) or step (b) is a viral vector.

6. The method of claim 1, wherein the vector of step (a) or step (b) is a plasmid.

7. The method of claim 1, further comprising
   (d) growing the mammalian dental epithelial cell on a mesh in order to form a multi-cellular tissue.

8. The method of claim 7, wherein the mesh comprises collagen matrix, sponge, nanoparticle mesh or scaffold, lipids, or fibers.

9. The method of claim 7, wherein the growing is for 2 to 10 weeks.

10. The method of claim 7, further comprising (e) implanting the multi-cellular tissue into the subject.

11. A mammalian dental epithelial cell that expresses amelogenin produced by the method of claim 1.

* * * * *

UNITED STATES PATENT AND TRADEMARK OFFICE
CERTIFICATE OF CORRECTION

PATENT NO. : 10,920,195 B2
APPLICATION NO. : 15/526282
DATED : February 16, 2021
INVENTOR(S) : Brad A. Amendt and Thad Sharp Page 1 of 1

It is certified that error appears in the above-identified patent and that said Letters Patent is hereby corrected as shown below:

In the Specification

Column 1, Line 14, please delete "DE13941" and insert -- DE013941 -- therefor.

Signed and Sealed this
Twenty-fifth Day of January, 2022

Drew Hirshfeld
*Performing the Functions and Duties of the*
*Under Secretary of Commerce for Intellectual Property and*
*Director of the United States Patent and Trademark Office*